US012594131B2

(12) United States Patent
Jacobsen et al.

(10) Patent No.: US 12,594,131 B2
(45) Date of Patent: Apr. 7, 2026

(54) SYSTEM AND METHOD FOR NAVIGATION

(71) Applicant: Medtronic Navigation, Inc., Louisville, CO (US)

(72) Inventors: Bradley W. Jacobsen, Erie, CO (US); Victor D. Snyder, Erie, CO (US); Andrew J. Wald, Fort Worth, TX (US)

(73) Assignee: Medtronic Navigation, Inc., Louisville, CO (US)

( * ) Notice: Subject to any disclaimer, the term of this patent is extended or adjusted under 35 U.S.C. 154(b) by 100 days.

(21) Appl. No.: 18/524,898

(22) Filed: Nov. 30, 2023

(65) Prior Publication Data

US 2025/0177053 A1    Jun. 5, 2025

(51) Int. Cl.
| | |
|---|---|
| *A61B 5/05* | (2021.01) |
| *A61B 34/20* | (2016.01) |
| *G06T 1/00* | (2006.01) |
| *G06T 7/00* | (2017.01) |

(52) U.S. Cl.
CPC ............ *A61B 34/20* (2016.02); *G06T 1/0007* (2013.01); *G06T 7/00* (2013.01); *A61B 2034/2051* (2016.02); *A61B 2034/2072* (2016.02); *G06T 2207/10132* (2013.01)

(58) Field of Classification Search
CPC ............ A61B 34/20; A61B 2034/2051; A61B 2034/2072; G06T 7/0007
See application file for complete search history.

(56) References Cited

U.S. PATENT DOCUMENTS

| | | | | |
|---|---|---|---|---|
| 5,538,004 | A | * | 7/1996 | Bamber ............... G01S 15/899 600/463 |
| 5,592,939 | A | | 1/1997 | Martinelli |
| 5,830,144 | A | | 11/1998 | Vesely |
| 5,913,820 | A | | 6/1999 | Bladen et al. |
| 5,983,126 | A | | 11/1999 | Wittkampf |
| 6,474,341 | B1 | | 11/2002 | Hunter et al. |
| 6,940,941 | B2 | | 9/2005 | Gregerson et al. |
| 7,001,045 | B2 | | 2/2006 | Gregerson et al. |
| 7,085,400 | B1 | | 8/2006 | Holsing et al. |
| 7,106,825 | B2 | | 9/2006 | Gregerson et al. |
| 7,108,421 | B2 | | 9/2006 | Gregerson et al. |
| 7,188,998 | B2 | | 3/2007 | Gregerson et al. |
| 7,751,865 | B2 | | 7/2010 | Jascob et al. |
| 8,175,681 | B2 | | 5/2012 | Hartmann et al. |
| 8,503,745 | B2 | | 8/2013 | Simon et al. |
| 8,737,708 | B2 | | 5/2014 | Hartmann et al. |
| 9,138,204 | B2 | | 9/2015 | Koenig et al. |
| 9,737,235 | B2 | | 8/2017 | Hartmann |
| 11,135,025 | B2 | | 10/2021 | Snyder et al. |
| 2002/0107445 | A1 | | 8/2002 | Govari |

(Continued)

OTHER PUBLICATIONS

International Search Report and Written Opinion received by the International Searching Authority for PCT/IB2024/061823 mailed Feb. 6, 2025.

(Continued)

*Primary Examiner* — Joel F Brutus
(74) *Attorney, Agent, or Firm* — Mueting Raasch Group

(57) ABSTRACT

Disclosed is a system for assisting in guiding and performing a procedure on a subject. The subject may be any appropriate subject such as a living or non-living subject or inanimate object and/or an animate object.

21 Claims, 14 Drawing Sheets

(56) References Cited

U.S. PATENT DOCUMENTS

| | | | |
|---|---|---|---|
| 2012/0245457 A1* | 9/2012 | Crowley | A61B 8/4477 |
| | | | 600/424 |
| 2012/0277585 A1 | 11/2012 | Koenig et al. | |
| 2019/0025040 A1* | 1/2019 | Andreason | A61B 5/062 |
| 2020/0187826 A1 | 6/2020 | Huffer et al. | |
| 2020/0196983 A1 | 6/2020 | Kruecker | |

OTHER PUBLICATIONS

International Search Report and Written Opinion received by the International Searching Authority for PCT/IB2024/061824 mailed Feb. 12, 2025.

International Search Report and Written Opinion received by the International Searching Authority for PCT/IB2024/061825 mailed Feb. 14, 2025.

Abdul G. Olabi et al., Design and application of magnetostrictive materials, Materials & Design, vol. 29, issue 2, 2008, pp. 469-483,, ISSN 0261-3069, https://doi.org/10.1016/j.matdes.2006.12.016.

Chengde Gao et al., Magnetostrictive alloys: Promising materials for biomedical applications, Bioactive Materials, vol. 8, Feb. 2022, pp. 177-195, publishing services by Elsevier B.V. on behalf of KeAi Communications Co. Ltd.

Magnetostrictive Position Sensors, Displacement sensor with shear wave technology for measuring the transit time difference between two points, MEGATRON Elektronik GmbH & Co. KG © 2024, https://www.megatron.de/en/category/magnetostrictive-position-sensors.html, retrieved on Feb. 28, 2024.

Magnetostrictive sensors, Reliable even for long distances and rough conditions, Balluff Inc. 2024, https://www.balluff.com/en-us/products/areas/A0001/groups/G0116, retrieved on Feb. 28, 2024.

PI Americas, Motion Control, Nanopositioning, Precision Positioning & Automation, Piezo Products, Comliance with Applicable Laws; Expert Control Laws, 1996-2024, https://www.pi-usa.us/en, retrieved on Feb. 28, 2024.

Piezo Direct Custom Piezo Ceramics, 2024 Piezo Direct, Burlingame, California, https://piezodirect.com, retrieved on Feb. 28, 2024.

R. Grossinger et al., Materials with high magnetostriction, IOP Conf. Series: Materials Science and Engineering, International Symposium on Advanced Materials, vol. 60, Sep. 23-27, 2023, Islamabad, Pakistan, DOI 10.1088/1757-899X/60/1/012002.

Wei Yan et al., Single fibre enables acoustic fabrics via nanometre-scale vibrations. Nature 603, 616-623 (2022), https://doi.org/10.1038/s41586-022-04476-9.

* cited by examiner

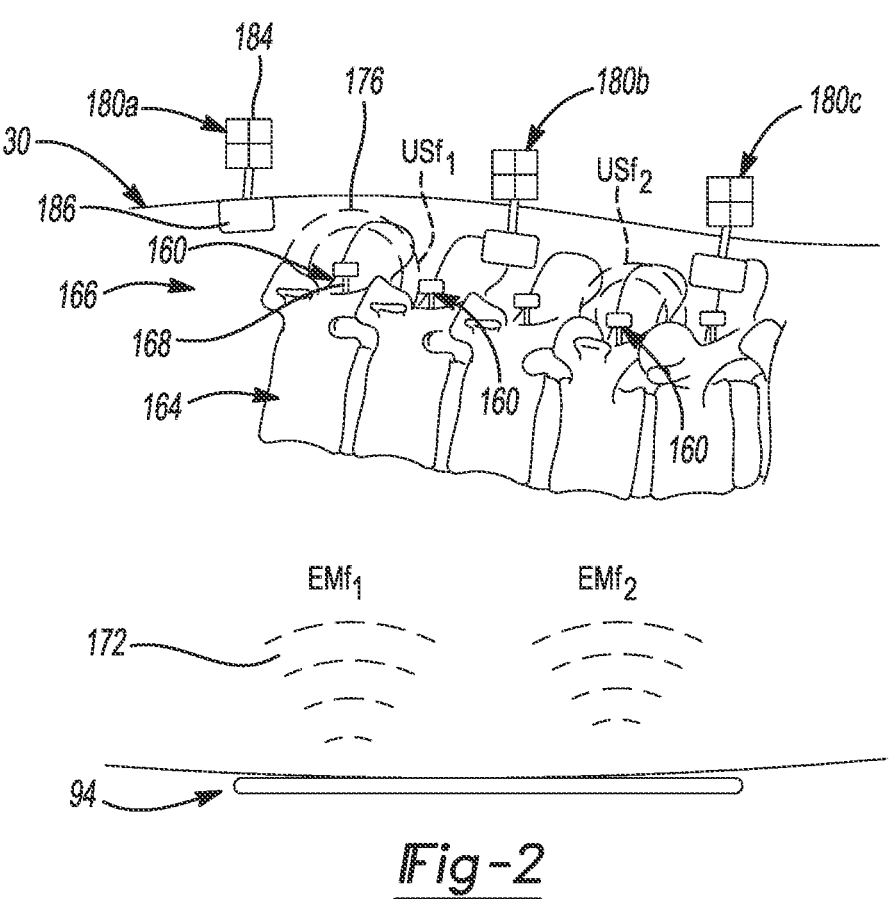
*Fig-2*
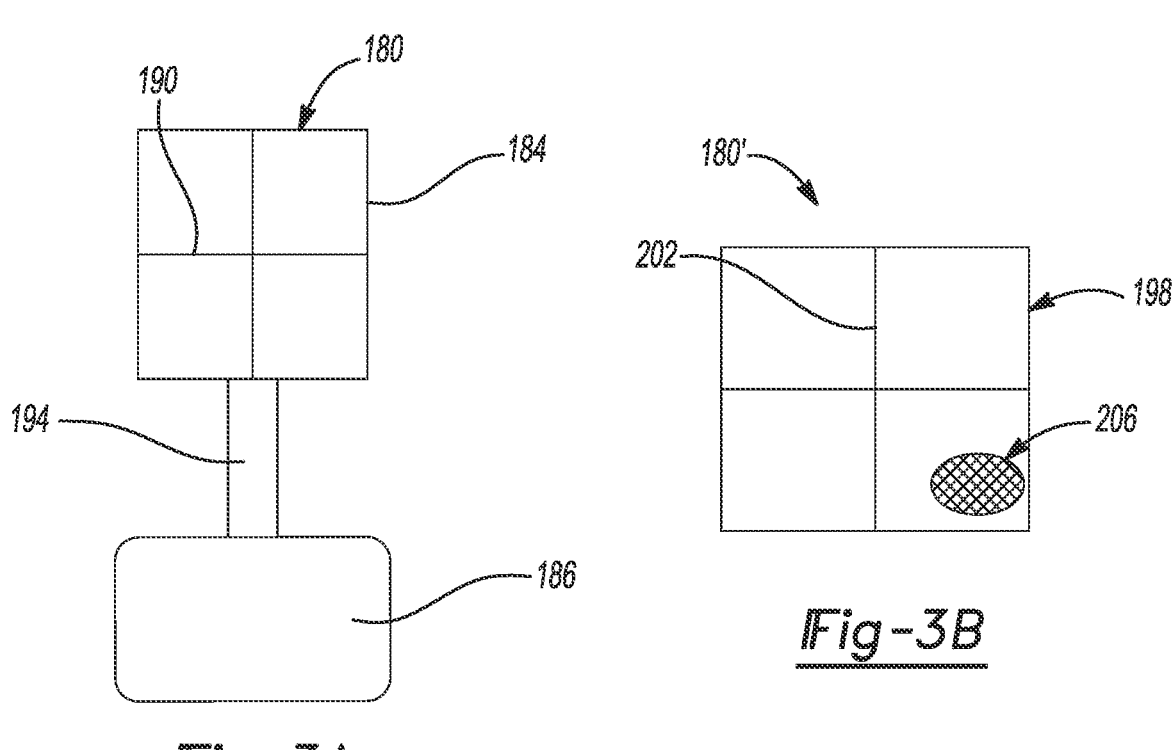
*Fig-3A*
*Fig-3B*

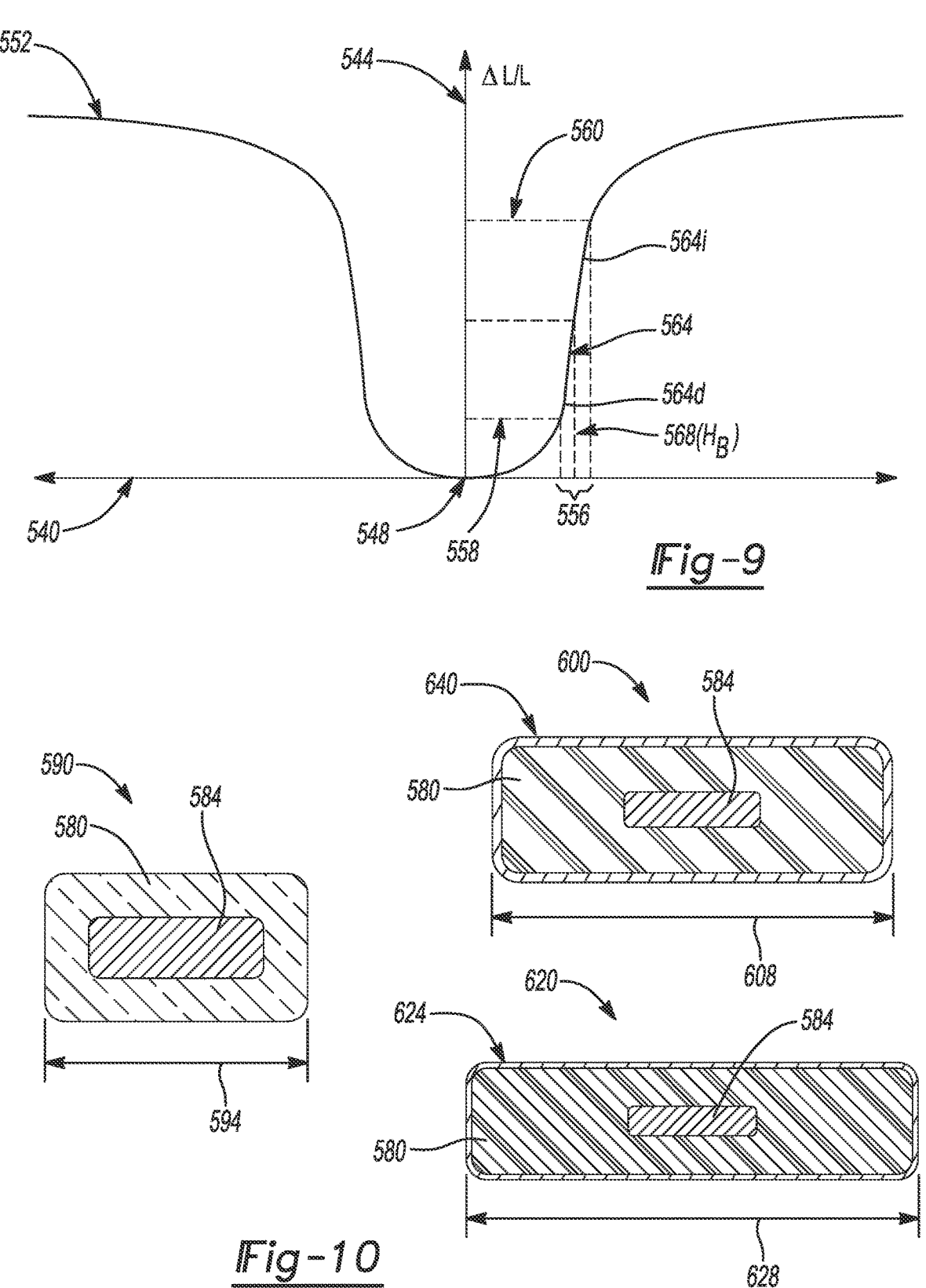
_Fig-9_
_Fig-10_

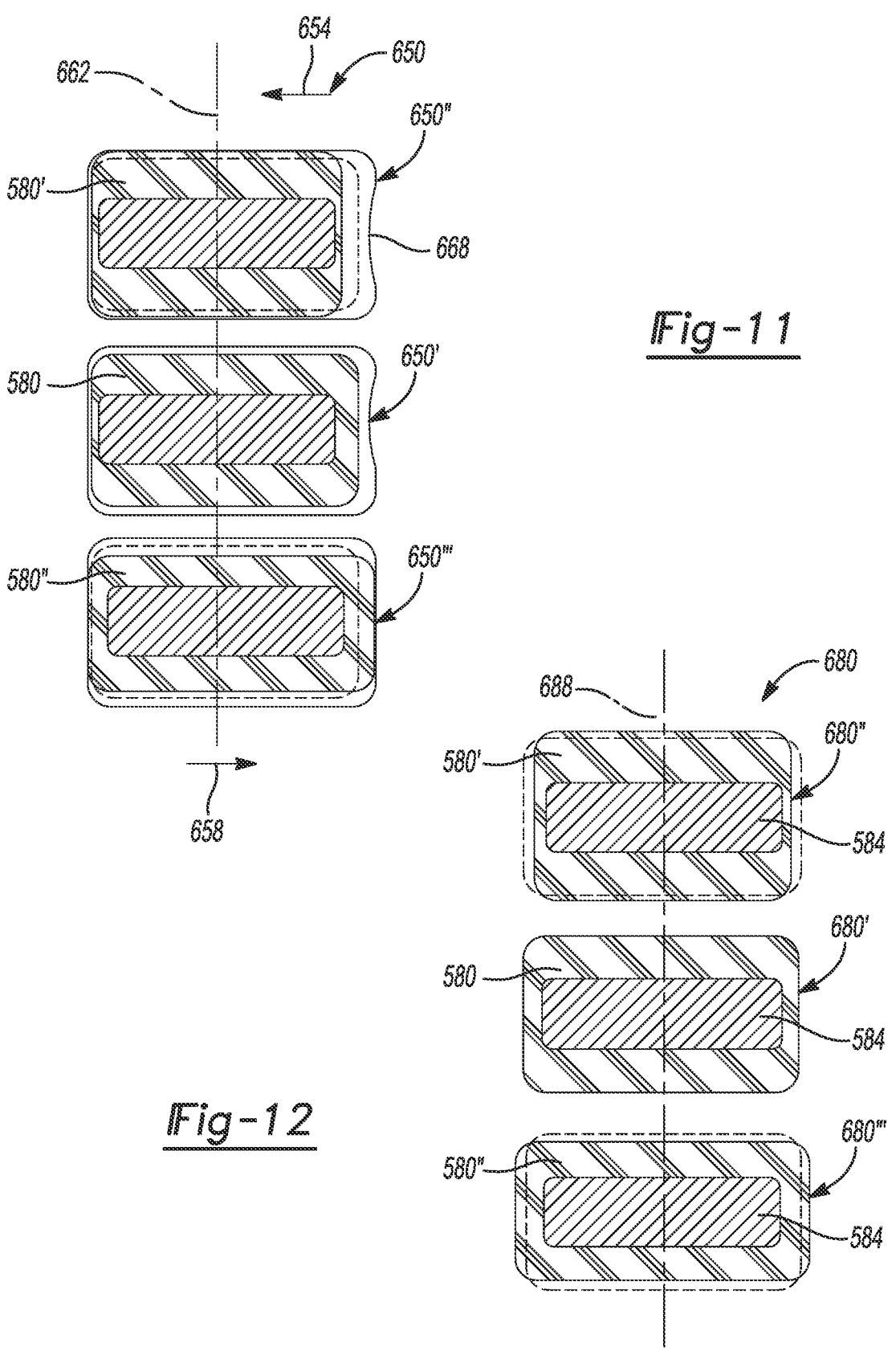
_Fig-11_
_Fig-12_

SYSTEM AND METHOD FOR NAVIGATION

CROSS-REFERENCE TO RELATED APPLICATIONS

This application includes subject matter related to the application Ser. Nos. 18/524,836 and 18/524,933. The entire disclosure(s) of (each of) the above application(s) is (are) incorporated herein by reference.

FIELD

The subject disclosure is related generally to a tracking and navigation system, and particularly to tracking using an electromagnetic field and related sensor.

BACKGROUND

This section provides background information related to the present disclosure which is not necessarily prior art.

An instrument can be navigated relative to a subject for performing various procedures. For example, the subject can include a patient on which a surgical procedure is being performed. During a surgical procedure, an instrument can be tracked in a physical space which may also be referred to as an object or subject space. In various embodiments, the subject space can be a patient space defined by a patient. The location of the instrument that is tracked can be displayed on a display device relative to an image of the patient.

The position of the patient can be determined with a tracking system. Generally, a patient is registered to the image, via tracking an instrument relative to the patient to generate a translation map between the subject or object space (e.g., patient space) and the image space. This often requires a user, such as a surgeon, to identify one or more points in the subject space and correlating, often identical points, in the image space.

After registration, the position of the instrument can be appropriately displayed on the display device while tracking the instrument. The position of the instrument relative to the subject can be displayed as a graphical representation, sometimes referred to as an icon on the display device.

SUMMARY

This section provides a general summary of the disclosure, and is not a comprehensive disclosure of its full scope or all of its features.

According to various embodiments, an imaging system may be used to acquire image data of a subject. The imaging system may include an ultrasound imaging system that includes an ultrasound (US) probe that generally includes an ultrasound transducer to emit and receive ultrasound frequencies. It is understood, however, that the imaging system may include separate components that emit and receive ultrasound frequencies.

A tracking system, such as a tracking system that emits an electromagnetic field, may be used to track one or more tracking devices. The tracking devices may be positioned on instruments (which may include procedure instruments, imagers, or other members) and tracked in a physical space also referred to as a patient space. The position of the tracking device and an instrument with which it is associated (e.g., attached to) may be displayed in an image representing the subject. For example, the determined position may be superimposed on a portion of the image.

An electromagnetic (EM) field may be emitted by an emitter or transmitter and may be sensed by an electromagnetic sensing device of the tracking device. According to various embodiments, the electromagnetic sensing device may include one or more coils of a conductive material or may include other sensors including but not limited to Hall effect, flux gate, magneto-resistive, tunnel junction, optical, microelectromechanical systems (MEMS), magneto-optical, sensors or may include combinations thereof. Various other materials, such as conductive, magnetic, or conductive and magnetic materials, may interfere with a field being sent by the sensor.

A navigation system may be used to register or after an image is registered to a navigation space. Thus, a pose of a tracked portion or member may be displayed relative to an image. Also, systems may be used where a patient is not registered to an image but where an imaging device is tracked so that a pose of the acquired image data and related image are tracked.

According to various embodiments, a tracking system may also include or alternatively include an ultrasound tracking system. With an ultrasound tracking system an ultrasound signal may be sent and received to determine a location or position, or together a pose, of a tracking device. A selected tracking device may include both an EM tracking device and a US tracking device. Further, according to various embodiments, a device may operate to receive and/or send both an EM field or signal and an US signal. Thus, at least two tracking systems may be registered together.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a schematic detailed view of a tracking device assembling and localizer relative to a subject, according to various embodiments;

FIG. 3A is a schematic illustration of a tracking device assembly, according to various embodiments;

FIG. 3B is a schematic view of a tracking device assembly, according to various embodiments;

FIG. 9 is a graphical illustration of an EMUST operation, according to various embodiments;

FIG. 10 is a schematic illustration of an EMUST, according to various embodiments;

FIG. 11 is a schematic illustration of a movement of a single sided EMUST, according to various embodiments;

FIG. 12 is a schematic illustration of a multiple sided EMUST, according to various embodiments;

Corresponding reference numerals indicate corresponding parts throughout the several views of the drawings.

DETAILED DESCRIPTION

Figure 1:
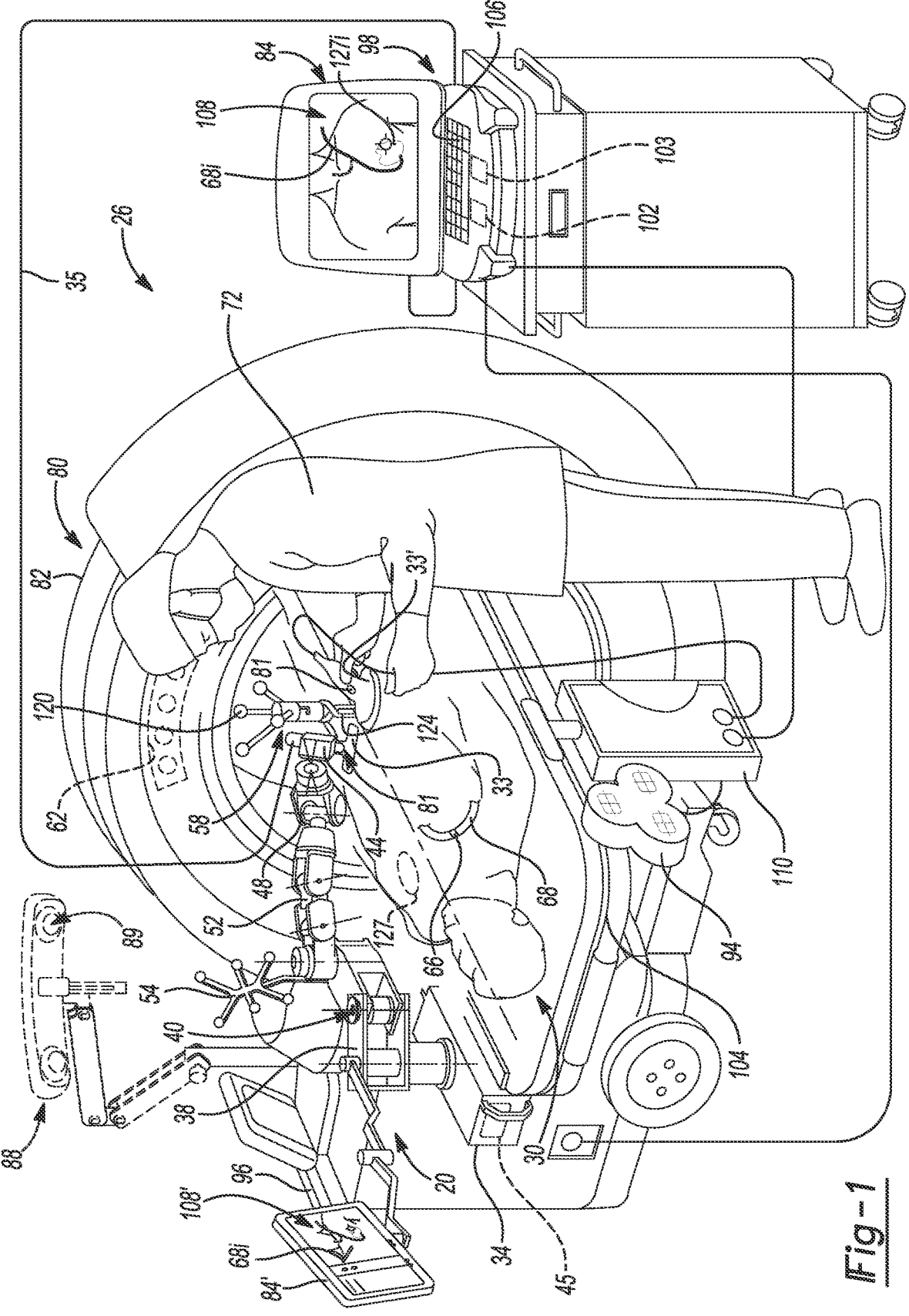
FIG. 1 is diagrammatic view illustrating an overview of a robotic system and a navigation system, according to various embodiments.

Example embodiments will now be described more fully with reference to the accompanying drawings.

The subject disclosure is directed to an exemplary embodiment of a surgical procedure on a subject, such as a human patient. It is understood, however, that the system and methods described herein are merely exemplary and not intended to limit the scope of the claims included herein. In various embodiments, it is understood, that the systems and methods may be incorporated into and/or used on non-animate objects. The systems may be used to, for example, to register coordinate systems between two systems for use on manufacturing systems, maintenance systems, and the like. For example, automotive assembly may use one or more robotic systems including individual coordinate systems that may be registered together for coordinated or concerted actions. Accordingly, the exemplary illustration of a surgical procedure herein is not intended to limit the scope of the appended claims.

Discussed herein, according to various embodiments, is a tracking system that may be used to track a selected tracking device. The tracking system may operate, according to various embodiments, by emitting an electromagnetic (EM) field from a localizer, also referred to as an EM localizer. The EM field may be emitted from one or more coils that may be oriented relative to an origin point. The coils may emit the field. The field may be a largely magnetic field. The field may be constant or varying in time. A tracking device may include one or more coils of conductive material that operate as sensors to sense the field. The field may generate a voltage or current within the coil of the tracking device. A determination of a position and orientation (also referred to collectively as a "pose") of the tracking device may be made based on a determination of the induced voltage or current from the field. It is further understood that an EM, or any appropriate tracking system, may operate by emitting a signal (e.g., EM fields) from the tracking device and receiving signals at the localizer.

Various materials are conductive or conductive and magnetic, such as conductive polymers, metal or metal alloys, or other materials. Objects or items may be formed with these materials. If an item formed with these materials is also in or near the field generated by the EM localizer, a current may be formed or induced or magnetization coerced in the object. In this instance, the object may be referred to as an interfering or target object. When a current is induced or a magnetization coerced in the interfering object, a field may also be produced. A field produced due to the induced current or coerced magnetization in the interfering object may also be referred to as an interfering field. These interfering fields may alter the field sensed by the tracking device such that it is not always sensing only the EM field generated by the EM localizer. The tracking device may sense both the EM field from the localizer and the EM field that is the interfering field. According to various theories, the sensed field may be a combination of both and/or the EM field from the EM localizer that is altered by the interfering field.

Various portions may be tracked relative to the subject. For example, a tracking system may be incorporated into a navigation system that includes one or more instruments that may be tracked relative to the subject. The navigation system may include one or more tracking systems that track various portions, such as tracking devices, associated with instruments. The tracking system may include a localizer that is configured to, alone or in combination with a processor, determine the pose of a tracking device in a navigation system coordinate system. Determination of the navigation system coordinate system may include those described at various references including U.S. Pat. Nos. 8,737,708; 9,737,235; 8,503,745; and 8,175,681; all incorporated herein by reference. In particular, a localizer may be able to track an object within a volume relative to the subject. The navigation volume, in which a device may be tracked may include or be referred to as the navigation coordinate system or navigation space. A determination or correlation between two coordinate systems may allow for or also be referred to as a registration between two coordinate systems.

Furthermore, images may be acquired of selected portions of a subject. The images may be displayed for viewing by a user, such as a surgeon. The images may have superimposed on a portion of the image can include a graphical representation of a tracked portion or member, such as an instrument. The images may have a coordinate system and define an image space. According to various embodiments, the graphical representation may be superimposed on the image at an appropriate position due to registration of an image space (also referred to as an image coordinate system) to a subject space. A method to register a subject space defined by a subject to an image space may include those disclosed in U.S. Pat. Nos. 8,737,708; 9,737,235; 8,503,745; and 8,175, 681; all incorporated herein by reference. In various embodiments, however, the imaging device may be tracked so its images may be tracked in a navigation space. In such a system a display of tracked instruments relative to tracked images without a tracked or registered patient may occur. Also, displaying tracked instruments and images relative to a tracked and registered patient.

The tracking of an instrument during a procedure, such as a surgical or operative procedure, allows for navigation of a procedure. When image data is used to define an image space it can be correlated or registered to a physical space defined by a subject, such as a patient as discussed herein. According to various embodiments, therefore, the patient defines a patient space in which an instrument can be tracked and navigated. The image space defined by the image data can be registered to the patient space defined by the patient.

The registration can occur with the use of fiducials that can be identified in the image data and in the patient space.

FIG. 1 is a diagrammatic view illustrating an overview of a procedure room or arena. In various embodiments, the procedure room may include a surgical suite in which may be placed a robotic system 20 and a navigation system 26 that can be used for various procedures. The robotic system 20 may include a Mazor X™ robotic guidance system, sold by Medtronic, Inc. The robotic system 20 may be used to assist in guiding a selected instrument, such as drills, screws, etc. relative to a subject 30. In addition or alternatively, the robotic system 20 may hold and/or move an imaging system, such as an ultrasound (US) probe 33 or 33'. The robotic system 20 may include a mount 34 that fixes a portion, such as a robotic base 38, relative to the subject 30. The robotic system 20 may include one or more arms 40 that are moveable or pivotable relative to the subject 30, such as including an end effector 44. The robotic arm 40 may be controlled by a selected robotic control module, which may be included with the navigation system or processor, as discussed herein, or a separate robotic control module 45. The robotic control module 45 may include one or more processors or memory that may communicate, execute instructions, or store instructions for operation of the robotic arm 40. The end effector may be any appropriate portion, such as a tube, guide, or passage member. Affixed to and/or in place of the end effector may be the imaging system that may be the US probe 33. The end effector 44 may be moved relative to the base 38 with one or more motors. The position of the end effector 44 may be known or determined relative to the base 38 with one or more encoders at one or more joints, such as a wrist joint 48 and/or an elbow joint 52 of the robotic system 20. One or more portions of the robotic system 20 may be formed of conductive materials.

The navigation system 26 can be used to track the location of one or more tracking devices and/or determine and/or illustrate a pose thereof. Tracking devices may include a robot tracking device 54, a subject tracking device 58, an imaging system tracking device 62, an imaging system or second imaging system tracking device 81, and/or an instrument or tool tracking device 66. A tool or moveable member 68 may be any appropriate tool such as a drill, forceps, catheter, or other tool operated by a user 72. The tool 68 may also be and/or an implant, such as a spinal implant or orthopedic implant. Further, the tool 68 may include one or more moveable portions, such as deployable portions. For example, a heart valve replacement and related inserter tool that may insert the instrument 68 or selected portion, such as an implant, into a heart 127 of the subject 30 and/or any other appropriate portion of any appropriate subject. It should further be noted that the navigation system 26 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 26 and the various instruments may be used in any appropriate procedure, such as one that is generally minimally invasive or an open procedure.

An additional or alternative, imaging system 80 may be used to acquire pre-, intra-, or post-operative or real-time image data of a subject, such as the subject 30. It will be understood, however, that any appropriate subject can be imaged and any appropriate procedure may be performed relative to the subject. In the example shown, the imaging system 80 comprises an O-Arm® imaging device sold by Medtronic Navigation, Inc. having a place of business in Colorado, USA. The imaging system 80 may have a generally annular gantry housing 82 in which an image capturing portion is moveably placed and/or enclosed. The imaging system 80 can include those disclosed in U.S. Pat. Nos. 7,188,998; 7,108,421; 7,106,825; 7,001,045; and 6,940,941; all of which are incorporated herein by reference, or any appropriate portions thereof. It is further appreciated that the imaging system 80 may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

The position of the imaging system 33, 80, and/or portions therein such as the image capturing portion, can be precisely known relative to any other portion of the imaging device 33, 80. The imaging device 33, 80, according to various embodiments, can know and/or recall precise coordinates relative to a fixed or selected coordinate system. For example, the robotic system 20 may know or determine its position and position the US probe 33 at a selected pose. The image data acquired with one or more ultrasound arrays of the US probe 33 may be registered in the navigation system such as disclosed in the U.S. Pat. Nos. 7,085,400 and 9,138,204, both incorporated herein by reference. Similarly, the imaging system 80 may also position the imaging portions at a selected pose. This can allow the imaging system 80 to know its position relative to the patient 30 or other references. In addition, as discussed herein, the precise knowledge of the position of the image capturing portion can be used in conjunction with a tracking system to determine the position of the image capturing portion and the image data relative to the tracked subject, such as the patient 30. In other words, the imaging system tracking device 62, 81 may be used and/or operable to determine a pose of the imaging system 33, 80 at a selected time such as during image data acquisition. The position of the imaging system, according to various embodiments, may be used for registration of an image space or coordinate system to a patient space or coordinate space. The robotic system may also be registered to one or more spaces or coordinate systems such as by the system and method as disclosed in U.S. Pat. No. 11,135,025, incorporated herein by reference.

Herein, reference to the imaging system 33 may refer to any appropriate imaging system, unless stated otherwise. Thus, the US probe 33 as the imaging system is merely exemplary regarding the subject disclosure. As one skilled in the art will understand, generally the US probe 33 may emit a US wave in a plane and receive an echo relative to any portions engaged by the wave. The received echo at the US probe 33 or other appropriate received may be used to generate image data and may be used to generate an US image also referred to as a sonogram.

The imaging device 80 can be tracked with the tracking device 62. Also, the tracking device 81 can be associated directly with the US probe 33. The US probe 33 may, therefore, be directly tracked with a navigation system 26 as discussed herein. In addition or alternatively, the US probe 33 may be positioned and tracked with the robotic system 20. Regardless, image data defining an image space acquired of the patient 30 can, according to various embodiments, be registered (e.g., manually, inherently, or automatically) relative to an object space. The object space can be the space defined by a patient 30 in the navigation system 26.

Additionally, an US transducer or a US receiver may receive a signal from the US probe 33. Further, a US tracking device may receive or emit an US signal that may be used for tracking. As discussed herein, for example, one or more US emitters and US receivers may be used to determine at least one degree of freedom of a pose of a portion associated with at least one of the US receivers or emitters.

The patient 30 can also be tracked as the patient moves with a patient tracking device, DRF, or tracker 58. Alternatively, or in addition thereto, the patient 30 may be fixed within navigation space defined by the navigation system 26 to allow for and/or maintain registration such as to the image space of the image 108. As discussed further herein, registration of the image space to the patient space or subject space allows for navigation of the instrument 68 with the image data. When navigating the instrument 68, a position of the instrument 68 can be illustrated relative to image data acquired of the patient 30 on a display device 84 such as with a graphical representation 68*i*, 68*i'*. Alternatively, the patient 30 may not be tracked or fixed and the system may track the instrument 68 relative to imaging device 33 and their associated images. An additional and/or alternative display device 84' may also be present to display an image. Various tracking systems, such as one including an optical localizer 88 or an electromagnetic (EM) localizer 94 can be used to track the instrument 68.

More than one tracking system can be used to track the instrument 68 or other portion, such as the US probe 33 with the tracking device 81 in the navigation system 26. According to various embodiments, these can include an electromagnetic tracking (EM) system having the EM localizer 94 and/or an optical tracking system having the optical localizer 88. In various embodiments, an ultrasound system may be used for tracking. Thus, a US localizer, as discussed herein, may be used with the navigation system 26 to determine at least one degree of freedom of a pose of a portion associated with a US tracking device. Either or both of the tracking systems can be used to track selected tracking devices, as discussed herein. It will be understood, unless discussed otherwise, that a tracking device can be a portion trackable with a selected tracking system. A tracking device need not refer to the entire member or structure to which the tracking device is affixed or associated.

The position of the patient 30 relative to the imaging device 33 can be determined by the navigation system 26. The position of the imaging system 33 may be determined, as discussed herein. The patient 30 can be tracked with the dynamic reference frame 58, as discussed further herein. Accordingly, the position of the patient 30 relative to the imaging device 33 can be determined.

Image data acquired from the imaging system 33, or any appropriate imaging system, can be acquired at and/or forwarded from an image device controller 96, that may include a processor module, to a navigation computer and/or processor module (also referred to as a processor) 102 that can be a part of a controller or work station 98 having the display 84 and a user interface 106. Further, a memory system or module 103, of any appropriate type, may be accessed by the processor 102. It will also be understood that the image data is not necessarily first retained in the controller 96, but may also be directly transmitted to the work station 98. The work station 98 can provide facilities for displaying the image data as an image 108 on the display 84, saving, digitally manipulating, or printing a hard copy image of the received image data. The user interface 106, which may be a keyboard, mouse, touch pen, touch screen or other suitable device, allows the user 72 to provide inputs to control the imaging device 80, 33, via the image device controller 96, or adjust the display settings of the display 84. The work station 98 may also direct the image device controller 96 to adjust the image capturing portion of the imaging device 80 to obtain various two-dimensional images along different planes in order to generate representative two-dimensional and three-dimensional image data.

With continuing reference to FIG. 1, the navigation system 26 can further include the tracking system including either or both of the electromagnetic (EM) localizer 94 and/or the optical localizer 88. The tracking systems may include a controller and interface portion 110. The controller 110 can be connected to the processor portion 102, which can include a processor included within a computer. The EM tracking system may include the STEALTHSTATION® AXIEM™ Navigation System, sold by Medtronic Navigation, Inc. having a place of business in Louisville, Colorado; or can be the EM tracking system described in U.S. patent application Ser. No. 10/941,782, filed Sep. 15, 2004, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 26 may also be or include any appropriate tracking system, including a STEALTHSTATION® TREON®, S7™, S8™ tracking systems having an optical localizer, that may be used as the optical localizer 88, and sold by Medtronic Navigation, Inc. of Colorado. With the optical localizer a camera or optical sensor 89 may sense a reflected or actively emitted optical signal, such as an infrared signal or a visible light signal such as from a selected object. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 80, etc. Alternatively, various portions, such as the instrument 68 may employ a wireless communications channel, such as that disclosed in U.S. Pat. No. 6,474,341, entitled "Surgical Communication Power System," issued Nov. 5, 2002, herein incorporated by reference, as opposed to being coupled directly to the controller 110. Also, the tracking devices 62, 66, 54 can generate a field and/or signal that is sensed by the localizer(s) 88, 94.

Various portions of the navigation system 26, such as the instrument 68, and others as will be described in detail below, can be equipped with at least one, and generally multiple, of the tracking devices 66. The instrument can also include more than one type or modality of tracking device 66, such as an EM tracking device and/or an optical tracking device. The instrument 68 can include a graspable or manipulable portion at a proximal end and the tracking devices may be fixed near the manipulable portion of the instrument 68.

Additional representative or alternative localization and tracking system is set forth in U.S. Pat. No. 5,983,126, entitled "Catheter Location System and Method," issued Nov. 9, 1999, which is hereby incorporated by reference. The navigation system 26 may be a hybrid system that includes components from various tracking systems.

According to various embodiments, the navigation system 26 can be used to track any appropriate portion such as the US probe 33 and/or the instrument 68 relative to each other or the patient 30. The instrument 68 can be tracked with the tracking system, as discussed above. Image data of the patient 30, or an appropriate subject, can be used to assist the user 72 in guiding the instrument 68. The image data may or may not be registered to the patient 30. For example, as discussed herein, the US probe 33 is tracked and generates the image data. Thus, as discussed above, the image data need not be registered to the subject to display a pose of the tracked instrument 68 relative to the image data generator with the tracked US probe 33. The image data defines the image space that is registered to the patient space defined by the patient 30. The registration can be performed as discussed herein, automatically, manually, or combinations thereof. The registration can include the process and the final transformation (including a translation and rotation) map. Generally, registration includes determining points in the image data and the subject space and determining a transformation map therebetween. Once done, the image space are registered to the subject space, or any two or more coordinate spaces.

Generally, registration also allows a transformation map to be generated of a tracked physical pose of the instrument 68 relative to the image space of the image data. The transformation map allows the tracked position of the instrument 68 to be displayed on the display device 84 relative to the image data 108. The graphical representation 68*i*, also referred to as an icon, can be used to illustrate the location of the instrument 68 relative to the image data 108.

With continuing reference to FIG. 1, a subject registration system or method can use the tracking device 58. The tracking device 58 may include portions or members 120 that may be trackable, but may also act as or be operable as a fiducial assembly. The fiducial assembly 120 can include a clamp or other fixation portion 124 and the imageable fiducial body 120. It is understood, however, that the members 120 may be separate from the tracking device 58. The fixation portion 124 can be provided to fix any appropriate portion, such as a portion of the anatomy. As illustrated in FIG. 1, the fiducial assembly 120 can be interconnected with a portion of a spine 126 such as a spinous process 130. The fixation portion 124 can be interconnected with a spinous process 130 in any appropriate manner. For example, a pin or a screw can be driven into the spinous process 130. Further, the tracking device 58 may be operable to track with one or more tracking systems or modalities, such as EM tracking system or optical tracking system.

As illustrated in FIG. 1, the imaging device 33 may include the US probe 33 that may be positioned relative to the subject 30, such as by the robotic system 20 and/or the surgeon 72. In various embodiments, the surgeon 72 may operate the robotic arm 20 and/or hold the US probe 33 separate therefrom. As discussed herein, therefore, the robotic system 20 may move the US probe 33 to a selected position relative to the subject 30. According to various embodiments, the imaging system may be positioned relative to the subject in any appropriate manner.

According to various embodiments, the ultrasound probe may emit or transmit ultrasound waves in a selected pattern or plane. The plane may be a shape as is understood by one skilled in the art. The plane is generally able to acquire data in a field of view to generate images, also referred to as sonograms when images are generated based on ultrasound data.

As discussed above, various tracking systems may be used with the navigation system 26 to allow for determination of a pose of a plurality of portions in a navigation space or volume. Various systems, such the EM tracking system including the localizer 94 may emit or generate an electromagnetic field. The field may be sensed by one or more items, such as the DRF 58 or the tracking device 66 to allow determination of the pose within the navigation space defined by the emitted field. Further, various other tracking systems may be operated, such as the optical tracking system including the localizer 88. As discussed above, various elements may be used to register the two tracking systems to one another, or co-register them to a selected portion, such as the image data 108 of the subject 30.

According to various embodiments, additional or alternative tracking systems may also be used or provided relative to the subject 30. The various tracking systems or elements may include an electromagnetic and ultrasound transducer (EMUST). An EMUST may include an EMUST 160 that may be associated with various portions of the subject 30, such as a vertebra 164 of a spine 166. In various embodiments, a plurality of EMUSTs 160 may be connected with a respective plurality of vertebrae 164. The image 108 may include segmented portions, such as segmented vertebra. Segmentation of the vertebrae may occur in any appropriate manner. Each of the segmented vertebrae in the image 108 may be correlated to a vertebra in the patient space. Thus, each of the EMUST 160 may relate to a segmented portion. The EMUST 160, according to various embodiments may include magnetostrictive materials and/or piezoelectric materials. Exemplary constructions include those sold by Cleaning Technologies Group, LLC having a place of business in Cincinnati, OH, Bluewave Ultrasonics having a place of business in Davenport, IA, 8125 Holton Dr., Balluf Inc. having a place of business at Florence, KY, MEGA-TRON Elektronik GmbH & Co. having a place of business at Munich, Germany, PI (Physik Instrumente) L.P. (e.g., U-628 Miniature Ultrasonic Motor Stage) having a place of business at Auburn, MA, PiezoDirect having a place of business at Burlingame, CA, and/or as described herein and/or combinations thereof.

As discussed herein, the EMUST 160 may be used to determine a real time pose of selected vertebra 164 and the image 108 may be updated with the tracked pose. For example, at least one EMUST 160 may be attached to a selected portion of the subject 30, such as a vertebra. Thus, a tracked pose of the EMUST 160 may be used to determine the pose of the portion to which it is attached. The tracked pose of the EMUST 160 and the determined pose of the portion to which is attached may be used to in real time update an image of that portion, including the image 108 of the subject 30.

The EMUST 160 may be attached or associated with the vertebra 164 in any appropriate manner, such as with a screw or fixation member 168. It is understood, however, that the EMUST 160 may be associated with the selected portion of the vertebrae 164 in any appropriate manner. Further, one skilled in the art will understand that the spine 166 may include a plurality of the vertebrae 164. Therefore, a plurality of the EMUST 160 may be associated with the plurality of vertebrae, such as one EMUST per vertebra. Also, the EMUST may be fixedly connected to, at least temporarily fixedly connected to, selected vertebrae. The EMUST 160 may move with respected vertebrae. The EMUST 160 may sense or receive energy from a field, such as a field generated by the localizer 94. As illustrated in FIG. 2, for example, the localizer 94 may emit a field EMF1 172. The EMUST 160 may receive or sense the field EMF1 (which may be an EM field) and thereafter emit or generate a signal, such as illustrated as an ultrasound signal or field USF1 176. The EMUST 160, therefore, may emit a field based upon the generated field from the localizer 94. As discussed above, the field generated by the localizer 94 may be an EM field.

The EMUST 160, briefly, may include various constructions including those discussed herein. The EMUST 160 may generally allow for a receiving of a EM field or an ultrasound signal and then thereafter emitting a EM field or an ultrasound signal. In various embodiments, the EMUST 160 may receive or sense an EM field and emit an US signal. Similarly, the EMUST 160 may receive or sense an US signal and emit an EM field. In other words, the EMUST 160 may transduce between the EM and US systems separately or simultaneously. Therefore, the EMUST 160 may be active in both an EM system and an ultrasound system. The EMUST 160, according to various embodiments, may be activated or stimulated by an EM field to generate an US signal, and vice versa. Further, the EMUST 160, or any appropriate tracking device or assembly, may be tracked in only one of any appropriate tracking system, such as the US tracking system or the EM tracking system. It is further understood, however, that the EMUST 160, or any appropriate tracking device or assembly, may be tracked in one or more of any appropriate tracking systems, such as the US tracking system or the EM tracking system.

The EMUST 160 that may be associated or connected to a selected portion of the subject 30, such as the vertebra 164, may emit a signal that is sensed by a selected assembly 180. The assembly 180 may be, according to various embodiments, a receiver assembly or also referred as a tracking assembly. As discussed herein, the assembly 180 may be provided according to various embodiments, including combinations of portions thereof. In various embodiments, the assemblies 180 may be positioned on a surface of the subject. The assemblies may be positioned at any appropriate position relative to the subject and may be operated to define a navigation space, a localizer assembly, or other features as discussed herein. The receiver assembly 180 may include an EM receiver 184 and an ultrasound receiver 186. The receiver assembly 180 may receive an EM field at the EM receiver 184 and an ultrasound signal at the ultrasound receiver 186. Therefore, for example, the assembly 180 may sense both an EM and an ultrasound signal emitted by the EMUST 160 or the localizer 94.

As illustrated in FIG. 2, one or more of the receiver assemblies 180 may be positioned relative to the subject 30. For example, a first receiver assembly 180a may be positioned relative to the spine 166 as may be two other assemblies 180b and 180c. One or more of the receiver assemblies 180 may be positioned relative to the subject at 30 to receive a signal or field from one or more of the EMUSTs 160. Therefore, a determination of at least one degree of freedom of a pose of each of the EMUSTs 160 may be made by receiving a signal by two or more of the receivers 180, such as by triangulation between the various portions.

In other words, a determination of one to six degrees of freedom of a pose of each of the EMUSTs 160 may be made by receiving a signal by one or more of the receivers 180. As an example, a US receiver 186 including one US transducer may receive an US signal at a time and so may determine one pose degree of freedom of the EMUST 160 such as a distance to the EMUST 160. As another example, three US receivers 186 each including one US transducer may receive an US signal at different times and so may triangulate three pose degrees of freedom of the EMUST 160, such as a distance and a direction to the EMUST 160. As another example, one US receiver 186 including a two dimensional array of US transducers may receive US signals at different times or phases across the array and so may fit three pose degrees of freedom of the EMUST 160, such as a distance and a direction to the EMUST 160. As another example, three or more US receivers 186 including one US transducer or one or more US receivers 186 including a two dimensional array of US transducers may receive US signals at different times or times and phases and of different strengths across each receiver and each array and so may fit six pose degrees of freedom of the EMUST 160, such as a distance and a direction and a relative orientation to the EMUST 160. It is understood that the various examples provided above may be applied to any one or more of the EMUSTs 160. Thus, at least one degree of freedom may be determined for one or more of the EMUSTs 160. The navigation system may have the processor module execute instructions for fitting the pose determination, as is understood by one skilled in the art.

With reference to FIG. 3A and FIG. 3B, the receiver 180 will be described in greater detail. With initial reference to FIG. 3A, the receiver 180 may include the EM receiver portion 184 and the US receiver portion 186. The EM receiver portion may include one or more conductive coil portions 190. The coil portions 190 may include conductive materials that may sense or be affected by the EM field 172. When sensing the EM field 172, a current or voltage may be induced within the conductive portion 190. A signal may be induced based upon the sensed field and may be received by the tracking system, such as at the EM controller 110 or the navigation system 26. The US receiver 186 may include a selected ultrasound receiving portion, such as generally known in the art. Exemplary ultrasound receiver systems may include those disclosed in Hu et al, "Single US transducer elements to Stretchable ultrasonic transducer arrays for three-dimensional imaging on complex surfaces", SCIENCE ADVANCES, Vol 4, Issue 3, 23 Mar. 2018 available at https://www.science.org/doi/10.1126/sciadv.aar3979 (DOI: 10.1126/sciadv.aar3979).

The EM receiver 184 and the ultrasound receiver portion 186 may be fixed relative to one another in any appropriate manner. For example, a connector or fixator 194 may be used to interconnect the two portions of the EM US receiver assembly 180. In various embodiments, the EM sensor or sensors may be printed or etched onto a layer (e.g., printed circuit board layer) directly above the US sensor layers. The EM sensor may be one or more traces (e.g., printed or etched) that may sense or emit an EM field. Therefore, a known position of the EM receiver 184 relative to the ultrasound receiver 186 may be known. The known pose may be predetermined and stored, such as in the memory module 103 for recall, during a selected procedure.

According to various embodiments, it is illustrated in FIG. 3B, the assembly 180 may be configured in various configurations. For example, an EM receiver portion 198 may include one or more conductive portions 202. The conductive portions 202 may operate similar to that discussed above. An ultrasound receiver portion 206 may be integrated into the EM receiver portion 198. Thus the ultrasound receiver portion 206 may be known relative to at least a portion of the EM receiver 198, and both may be defined or include a single origin or point. Therefore, again, the pose relationship of the EM receiver 198 and the ultrasound receiver 206 may be known for the receiver assembly 180'.

Accordingly, as discussed herein, the receiver assembly 180, according to various embodiments, may include any appropriate configuration and the illustrated configurations are merely exemplary. Nevertheless, the relative pose of the EM receiver and the US receiver may be known at a selected time, such as prior to a navigation portion or a procedure.

In various embodiments, a relative pose of the EM receiver portion and the US receiver portion may be determined during manufacturing, prior to a navigation in the procedure room, or the like. Nevertheless, the known pose of the two receivers relative to one another may allow for registration of an EM navigation space and the ultrasound navigation space. The receiver 180 may allow for a co-registration or registration of the two tracking systems relative to one another. As the two tracking systems are registered to one another they may be co-registered to other spaces, such as an image space defined by the image 108. Therefore, a tracked pose of a tracking device, such as the EM tracking device 66, may be known in both of the EM tracking space and the ultrasound tracking space, and other registered spaces, such as the image space. This may allow the instrument 68 to be tracked in either or both of the tracking systems and illustrated on the display 84 as the graphical representation 68*i*.

The receivers 180 allow for a co-registration of at least the two tracking systems. As discussed herein, the EM localizer 94 may generate a field. The EMUST 160 may generate an ultrasound field or signal that may be sensed by the US receivers 186. The generated US signal from the EMUST 160 may be sensed at the receiver assemblies 180 to allow for triangulation relative thereto, such as with a plurality of the EM/US receivers 180 as illustrated in FIG. 2. Therefore the US tracking system may also be used as a tracking system within the subject space, such as to track a pose of the vertebra 164 relative to the receiver assemblies 180.

As discussed above, the EM receiver portion 184 may be registered to the EM tracking system, such as with the field generated by the localizer 94, and the co-registration therefore allows the triangulated or determined pose of the EMUST 160 using the ultrasound signal that is received at the US receiving portion 186 of the assembly 180.

As discussed above, the EM/US receiver may have known positions relative to one another, as exemplarily illustrated in FIG. 3A and FIG. 3B. Thus the known position of the two receivers relative to each other may allow for respective tracking systems to be registered to one another by having a common origin or determinable (e.g., knowing) a common point in both tracking systems. As discussed above, the EM receiver 184 may be operated in an EM localizer or tracking system and to the ultrasound receiver 186 may be operated in a ultrasound or US localizer tracking system.

Figure 4:
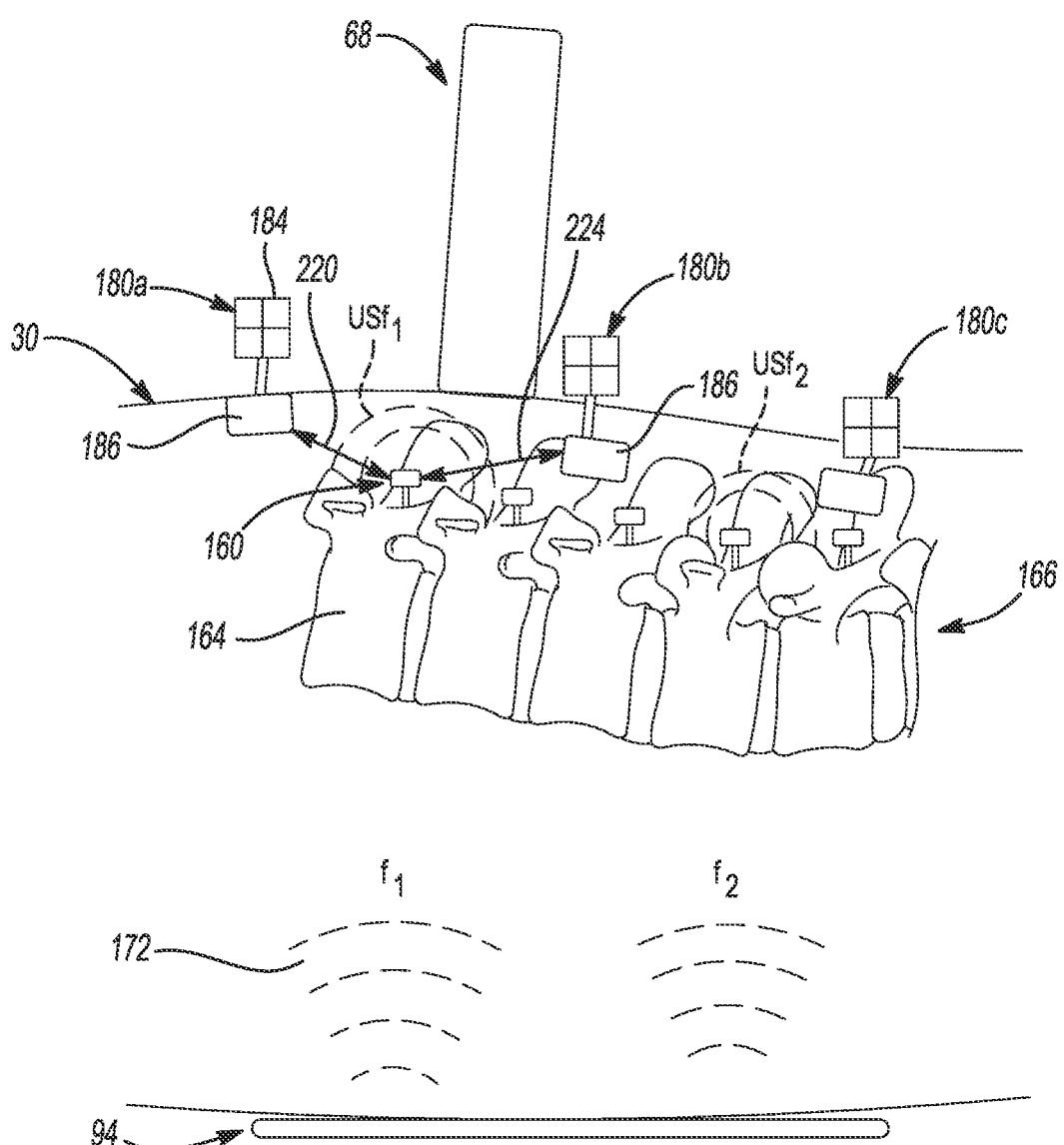
FIG. 4 is a schematic illustration of an instrument positioned relative to a subject having tracking device assemblies.

Such co-registration may assist in navigating a procedure relative to the subject 30. For example, as illustrated in FIG. 4, the EMUST 160 may be connected to the subject 30 such as at the vertebrae 164. The instrument 68 may be any appropriate instrument, and in various embodiments may include one or more magnetic or conductive portions. The instrument 68 or any other portion, such as an implant, imaging system, or the like when introduced into the field, such as the field 172 emitted by the localizer 94 may cause an interference. As understood by one skilled in the art, the field 172 may induce an Eddy current in the instrument 68. The Eddy current in the instrument 68 may generate or emit an interfering field or effect the field 172 emitted by the localizer 94. Thus, a tracked position, such as with the EM receiver 184 of the assembly 180*a* may be affected due to the presence of the instrument 68 or any other interfering portion.

In various examples, further, the EM trackers 184 may not be affected by the instrument 68 or some other conductive member positioned relative to the subject in the navigation space. A thin instrument 68 near or in between the vertebra 164 may affect a tracking device on a vertebra that operates only in the EM navigation system. Such a device, however, would not affect the US signaling of the EMUST 160 when used as a vertebral tracker. As a further example, the EM trackers 184 may be affected by the instrument 68. If instrument 68 or its position relative to the EM tracker affects EM tracker 184 on EM/US tracker 180*a* the EM/US registration may be maintained due to the use and tracking of the EM/US trackers 180*b* and 180*c* and maintain EM/US tracker 180*a* pose via US signals from EMUST 160 to 180*a* as well as 180*b* and 180*c*.

However, as illustrated above, the EM/US receiver assembly 180 may include the US receiver 186 fixed relative to the EM receiver 184. Therefore, a signal received with the US receiver 186 may be used to determine a pose of the selected portion, such as the vertebrae 164. As the EMUST 160 may emit an ultrasound signal the ultrasound signal will not be affected and/or not affect the instrument 68 in a manner that would interfere with determining a pose of the EMUST 160 which may be connected to the vertebra 164. Therefore, the ultrasound signal may be received by one or more of the ultrasound receivers, such as an ultrasound receiver of the EM/US receiver assembly 180*a* and the ultrasound receiver 186 of the EM/USB receiver assembly 180*b*. As is understood by one skilled in the art, according to various embodiments, at least one degree of freedom of a pose of the EMUST 160 may be determined by triangulating or determining at least two distances, such as a first distance 220 and a second distance 224 between the EMUST 160 and the respective EM/US receivers 180*a*, 180*b*. The use of the US signal to determine a pose or at least a selected degree of freedom of the pose may be selected based on various parameters. For example, the EM navigation system may be used to track the pose unless a selected amount of interference is determined. Interference may be determined in various manners, as understood by one skilled in the art.

The ultrasound tracking system, therefore, may be used to determine the pose of the vertebra 164. For example, a time of travel between the EMUST 160 and the respective EM/US receivers 180*a*, 180*b* may be used to calculate the first and second distances 220, 224. The navigation system 26 may calculate the distances based on known parameters. As the distances may be calculated to the EM/US receivers 180*a*, 180*b* and the EM/US receivers 180*a*, 180*b* are co-registered with the US and the EM navigation space, a determined pose in one navigation space may be transformed to the other.

In various embodiments, the US tracking system may include one or more receivers according to various configurations. For example, if the US receivers 186 is a single receiver (e.g., single transducer elements) it may resolve distances 220 and 224. That is one transducer element may be able to determine a distance from one US emitter. If the US receiver 186 is an array of US transducers (e.g., arrayed transducer elements) the array may allow one or two dimensional phased array signaling that may resolve distances 220 and 224 and directions to the transmitters at or along the distances 220 and 224 (e.g., illustrated as the double headed arrows) so that a single arrayed US receiver 186 may localize the EMUST 160.

The ultrasound tracking system may operate similar to the other tracking systems, as noted above. The ultrasound tracking system may have one or more portions that are used to generate signals relative to one another. As is known in the art, the ultrasound tracking signals may be used to triangulate and/or determine a position relative to one another. For example, an ultrasound wave may pass at known speeds through selected tissues or selected density of materials. The signals may be received from the EM/US receivers 180 in any appropriate manner, such as a wired/wireless manner. A selected processor, such as the navigation system 26 processor 102, may then execute instructions to determine a pose or distance relative to one or more of the US receivers 186. It is further understood that other US receivers may be used to assist in tracking various portions, such as within the subject 30. As discussed above an ultrasound probe 33 may be associated with the robotic arm system 20 in/or an ultrasound probe 33' may be used by the user 72. Accordingly, an ultrasound transducer or receiver may be positioned at any appropriate position relative to the subject 30 to assist in receiving and/or sending an ultrasound signal to areas, portions, such as the EMUST 160.

Figure 5:
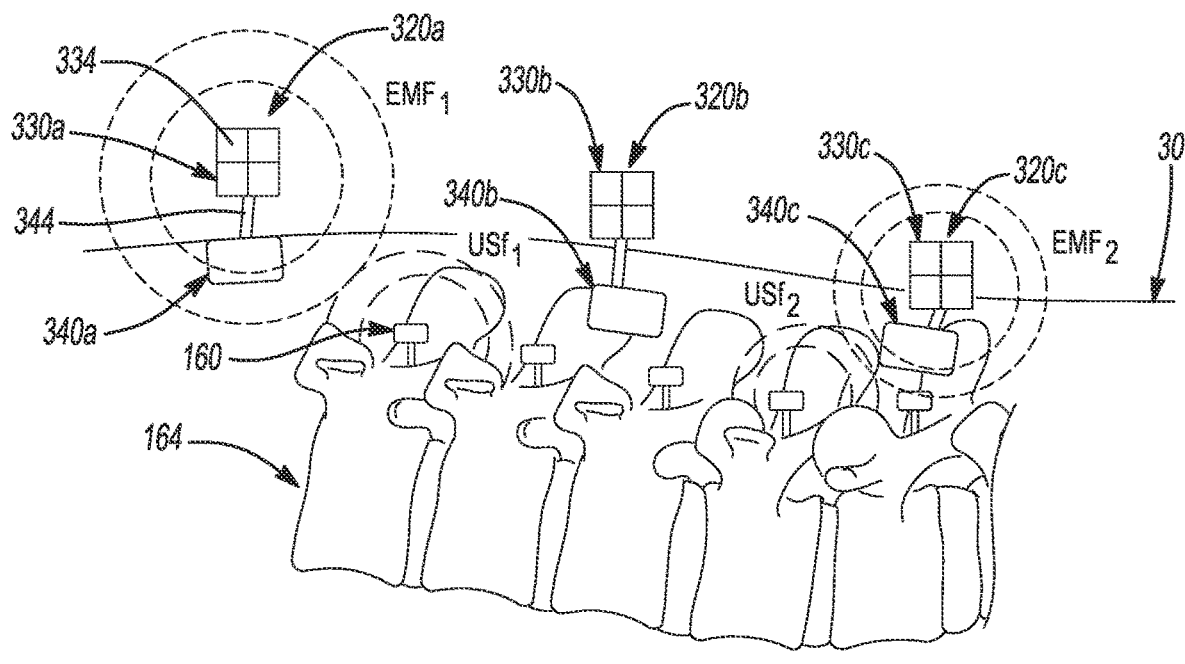
FIG. 5 is a schematic view of a tracking device assembly positioned relative to a subject.

Turning reference to FIG. 5, the subject 30 may have one or more of a transmitter and receiver (e.g., a transceiver) assembly 320 associated therewith that may have portions and/or operate in a manner similar to the assembly 180. According to various embodiments, the transceiver assembly 320 may be provided as one or plurality of transceiver assemblies including the transceiver assembly 320a, transceiver assembly 320b, and transceiver assembly 320c. The transceiver 320 may operate as ultrasound receivers in addition to EM transmitters and receivers or transceivers. In various embodiments, the transceiver assemblies 320 may be positioned on the subject 30 such as being positioned on a surface, such as a skin surface of the subject 30 similar to the EM/US receivers discussed above. The assemblies 320 may be operated to assist in localizing various portions, such as the EMUST 160, co-registering two or more navigation spaces, and/or defining a navigation space, as discussed herein.

Each of the EM/US transceivers 320 may include various components such as an EM transceiver 330. The EM transceiver 330 may include one or more portions, such as a conductive coil portion 334 that may either or both transmit an EM field or sense an EM field. The EM transceiver 330 may transmit a field, such as an EM field EMF 1 and/or sensor a field such as the transceiver assembly 320a sensing the field EMF 2 from the transceiver assembly 320c. The transceiver assembly 320, including the transceiver assembly 320a may also include an ultrasound receiver 340. The ultrasound receiver 340 may be similar to the ultrasound receiver discussed above, such as the ultrasound receiver 186 included with the EM/US receiver assembly 180.

According to various embodiments, therefore, the assembly 320 may include the EM transceiver 330 fixed relative to the US receiver 340 with a selected connection, such as the connection 344. In various embodiments, the EM transceiver 330 may be fixed relative to the US receiver 340 as a separate unit or incorporated therewith, according to various embodiments, as illustrated in FIG. 3A and FIG. 3B. Thus, the assembly 320 may be associated with the subject 30 to allow for emitting or sensing an EM field and receiving an US signal.

According to various embodiments, the assembly 320 may be associated with the subject in any appropriate manner. In various embodiments, each of the assemblies 320 may be associated with the subject 30 in a substantially random or unknown manner prior to positioning relative to the subject. Therefore, each of the assemblies 320 may emit a signal or field that is sensed by the other of the assemblies

320. For example, the first assembly 320a may emit a field EMF 1 that is sensed by either or both of the assemblies 320b and the assembly 320c. Similarly, the assembly 320c may emit the field EMF 2 they may be sensed by both of the assemblies 320a and 320b. This allows all of the assemblies 320 to be localized or co-registered relative to one another. Further, as the US receivers 340 are associated with each of the respective EM transceivers 330a-c the pose of the respective US receivers may also be known and co-register both the EM and US navigation spaces.

When including the EM transceiver assemblies 320, a separate EM localizer is not required to generate or define a navigation space. The EM transceiver 330 may both emit and sense a field to determine a pose of each of the transceivers relative to one another. Therefore, the pose of any EM tracking device relative to the assemblies 320 may also be determined. Similarly, as discussed above, the US receivers are also known relative to the EM transceivers 330. This allows the two navigation spaces to be registered and co-localized relative to one another. Again the co-localization or co-registration may be performed without requiring a separate EM localizer, such as the EM localizer 94.

One or more of the EMUST 160 may be associated with various portions of the subject 30. As illustrated in FIG. 5, the EMUST 160 may be fixed to the vertebra 164. The subject 30 may include a plurality of vertebrae to which each may be attached one or more of the EMUSTs. Again the EMUST 160 may emit an ultrasound signal that may be sensed or received as to the US receiver 340. Thus, a pose of the vertebrae may be determined by receiving the US signal at one or more of the US receivers. For example, as discussed above, the US signal US F1 may be received by both the US receiver 340a and US receiver 340b. The pose of the EMUST 160 may be determined by triangulating the signal from both of the US receivers 340a, 340b.

According to various embodiments, each of the transmitters may transmit in one or more frequencies. For example, each of the EMUSTs may transmit in a plurality of frequencies to distinguish one from another at each of the US receivers 348. Similarly, each of the EM transceivers 330 may transmit in one or more frequencies to distinguish one another during a co-localization or co-registration. Also, the multiple frequencies may allow for operating each of the elements substantially simultaneously, while allowing for a distinguishing or distinguishment of each of the portions relative to one another, such as each of EMUSTs separate from one another and each of the EM transceivers separate from one another. According to various embodiments, however, the system may also allow for time multiplexing where signals may be transmitted at different times to allow for distinguishing there between.

Figure 6:
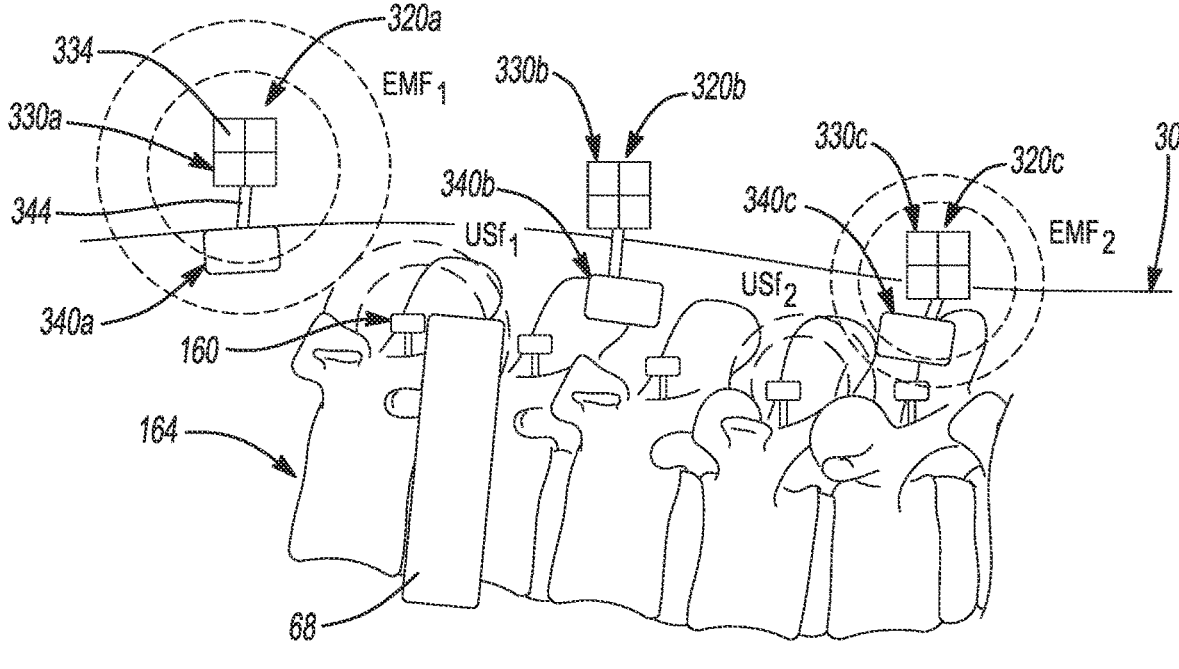
FIG. 6 is a schematic view of a subject with a device positioned relative thereto.

Turning to reference to FIG. 6, the instrument 68 may be positioned relative to the subject 30, such as near or adjacent to the vertebrae 164. Again the instrument 68 may be tracked in any appropriate navigation system, such as an EM navigation system. The instrument 68 may, in various embodiments, include elements or portions that may distort or be an interfering object in an EM navigation system. Therefore, the EMUST 160 may generate the ultrasound signal, such as US f1, that may be sensed to receive at the receivers 340. Receiving the US signal at the receiver 340 would generally be not affected by any magnetic or conductive material of the instrument 68. Accordingly, a pose of the vertebrae 164 may be effectively tracked in the US navigation space. Again receiving the signal at the receivers 340 which are associated with one or more of the EM transceivers 330 thus allowing a co-registration or co-localization of the US and EM navigation space may allow for a determination of a pose of the vertebrae 164 in an EM space even when only the US signal USF 1 is transmitted. The signal and pose determination may not be affected by any interfering portion of the instrument 68.

The operation of the navigation system with the assemblies 320 may be substantially similar to the system of the assembly 180 discussed above. The operation and co-registration or co-localization of the US and EM navigation spaces may occur in a substantially similar manner. While the localizer 94 may be operated to energize the EMUST 160 in/or to define a navigation space, the EM transceivers 330 may operate in a substantially similar manner for the assemblies 320. The navigation space may also be defined by the plurality of the EM transceivers 330 rather than the single EM localizer 34. Each of the EM transceivers 330, however, may be operated and together perform or operate as a localizer array or system once each of the EM transceivers 330*a-c* are localized relative to one another such as they are receiving their respective or sensing the respective EM fields from each of the transceivers.

Figure 7:
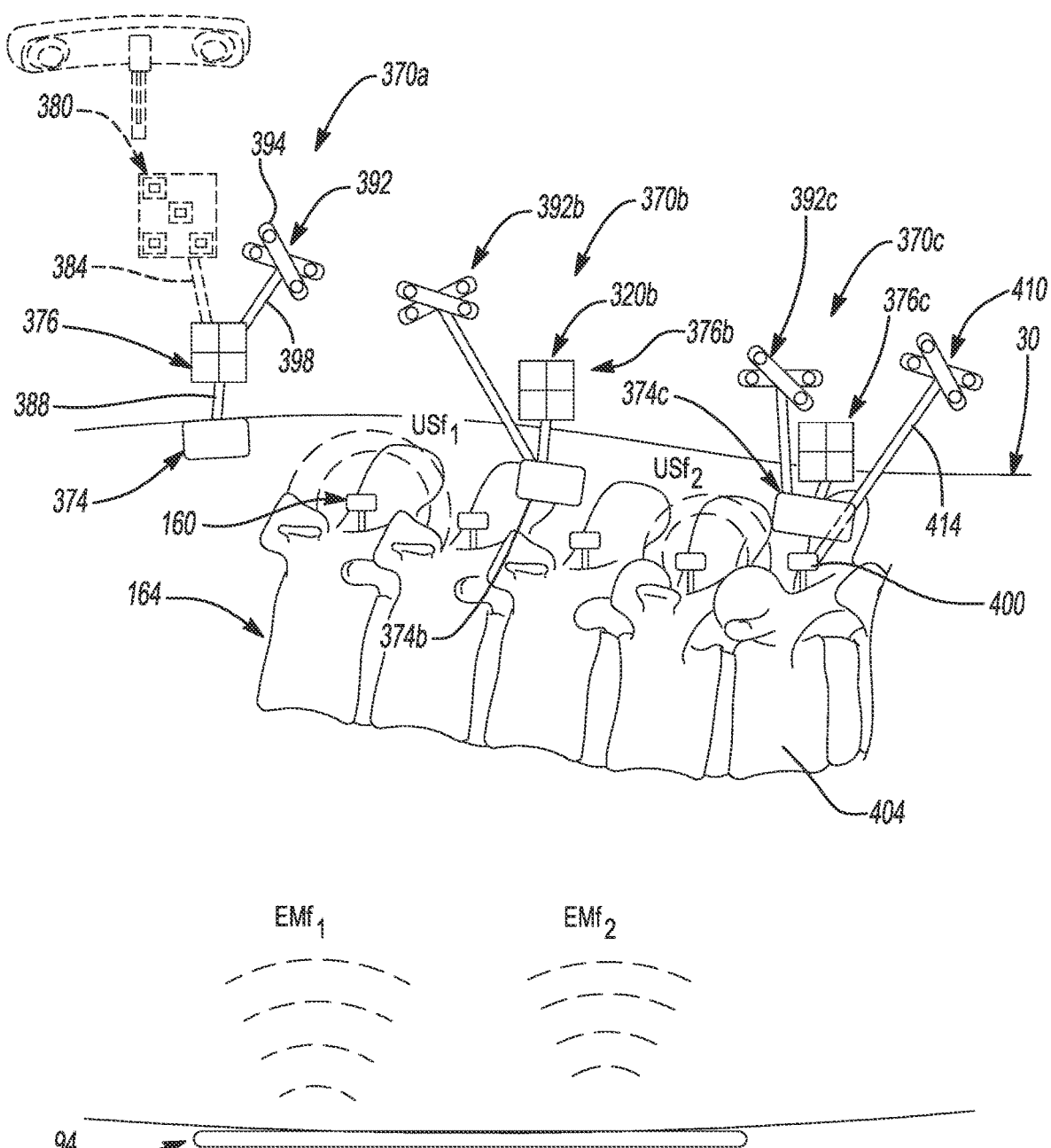
FIG. 7 is a schematic view of a subject having tracking device assemblies positioned relative thereto, according to various embodiments.

Turning reference to FIG. 7, portions of the navigation system 26 may be associated with various portions of the subject 30. As discussed above, one or more EMUSTs 160 may be associated with the subject 30, such as being connected with the vertebra 164. The localizer 94 may emit one or more fields at one or more frequencies, such as EMF 1 and EMF 2. Further, associated with the subject, such as affixed to an external surface thereof, may be one or more tracking or localizer assemblies 370. The tracking or localizer assembly 370 may include a plurality of elements that are associated with one another, such as connected together and/or formed together.

According to various embodiments, the assembly 370 may include an ultrasound receiving portion 374. The ultrasound receiving portion may be affixed to the subject to 30 in an appropriate manner, such as with an adhesive patch. Included with and/or connected to the ultrasound receiver 374 may be an EM portion 376. As discussed above, the EM portion 376 may be a receiver, transmitter, or a transceiver similar to the EM transceiver 330 as discussed above.

Also connected to, such as directly or interconnected with the US receiver 374 may be one or more optical tracking portions. For example, a first optical tracking member 380 may include a graphic that may be viewed by one or more optical tracking assemblies, such as the optical localizer 88, to understand the pose of the optical tracker 380. The pose of the optical tracker may be related to the US receiver 374 by having the optical tracker 380 connected to the US receiver 374 with a connection member 384. The connection member 384 may be directly connected to the US receiver or interconnected to the US receiver, such as being connected to the EM portion 376 that is also connected with a connector 388 to the US receiver 374. Nevertheless, the optical localizer 88 may be used to determine a pose of the optical tracking portion 380.

Additionally, or alternatively, an optical tracker 392 may be associated with the assembly 370. The optical tracker 392 may include optical portions, such as reflective members 394 that may be provided in a selected array or shape. Again, the optical tracking portions 394 may be viewed or imaged with the optical localizer 88 to determine a pose of the optical tracking member 392. The optical tracking member 392 may be connected with the US receiver 374 with an appropriate connector, such as the connector 398 and/or formed directly therewith.

As noted above, various tracking portions may be assembled into a single unit. In various embodiments, the assembly 370 may include a graphical portion 380 printed on the US receiver 374 to allow for the optical localizer 88 to view the optical member 380 to determine a pose of the US receiver 374. Accordingly, the various interconnections illustrated in FIG. 7 are not required, but may be used as an example of the interconnection and the relatability of the various tracking portions. Therefore, the tracking assembly 370 may be used to track and corelate various and multiple tracking systems such as an optical tracking system, an EM tracking system, and an ultrasound tracking system.

In various embodiments of plurality of the assemblies may be provided, including the assembly 370*b* and the assembly 370*c*. Each of the assemblies may include at least a US receiver portion 374*b* and *c*, respectively, an optical tracking portion 392*b* and *c*, respectively, and an EM tracking portion 376*b* and *c*, respectively. Each of the tracking localizer assemblies 370*a*, 370*b*, and 370*c* may be associated with the subject 30 in an appropriate manner. For example, each may be affixed to an exterior portion of the subject 30. Further, each may be used to track or localize a portion that is connected to a separate portion of the subject, such as the EMUST 160 connected to the vertebrae 164. As discussed above, each of the assemblies 370 assembly may be localized in the EM tracking system with the separate localizer 94 or relative to one another by receiving and transmitting respective fields. Thus, the various assemblies 370 may be used to correlate a plurality of the tracking assemblies relative to one another.

Again, as discussed above, the EMUST may be connected to one or more other vertebrae. As illustrated in FIG. 7, the EMUST 160 may be connected to the vertebra 164. Similarly, an EMUST 400 may be connected to a vertebra 404. The two vertebrae 164 and 404 may be interconnected in the spine of the subject 30. The EMUST 400 may be used to track or determine the pose of the vertebrae 404 substantially directly by being connected thereto. In various embodiments, an optical tracking portion 410 may also be connected with the EMUST 400. Therefore, the EMUST 400 may be directly associated or correlated with an optical tracking system, in a manner as similarly discussed above. A connector 414 may be used to interconnect to the optical tracking portion 410 to the EMUST 400. Therefore, posed the EMUST 400 may be known with the optical tracking system substantially directly due to the connection of the optical tracking number 410 to the EMUST 400.

Regardless, the EMUST 400 may be activated, such as with a signal from the localizer 94. The EMUST, according to various embodiments, including the EMUST 160 and the EMUST 400 may then emit an ultrasound signal, such as the first ultrasound signal USF 1 or second ultrasound signal USF 2. Differing frequencies from the localizer may cause the EMUST to emit different frequencies of ultrasound signals. The ultrasound signals emitted by the EMUSTS may be determined in the US navigation space, such as by triangulation to various one of the US receivers of the assemblies 370. Thus, the pose of the vertebrae 164, 404 may be determined substantially directly in the US navigation space. The US navigation space may be co-registered and co-localized to other navigation spaces, such as an EM or optical navigation system, due to the inclusion of the optical and EM portion within the tracking assemblies or localizing assemblies 370.

Similarly, an instrument may be positioned relative to one or more of the vertebrae that may not interfere with the signal that is an ultrasound signal. The instrument may interfere with other portions, such as in the EM system, but by positioning the assembly 370 away from an area of operation, such as that the vertebrae 164, the instrument may not interfere with a signal emitted by the EMUST 160, 400.

Figure 8:
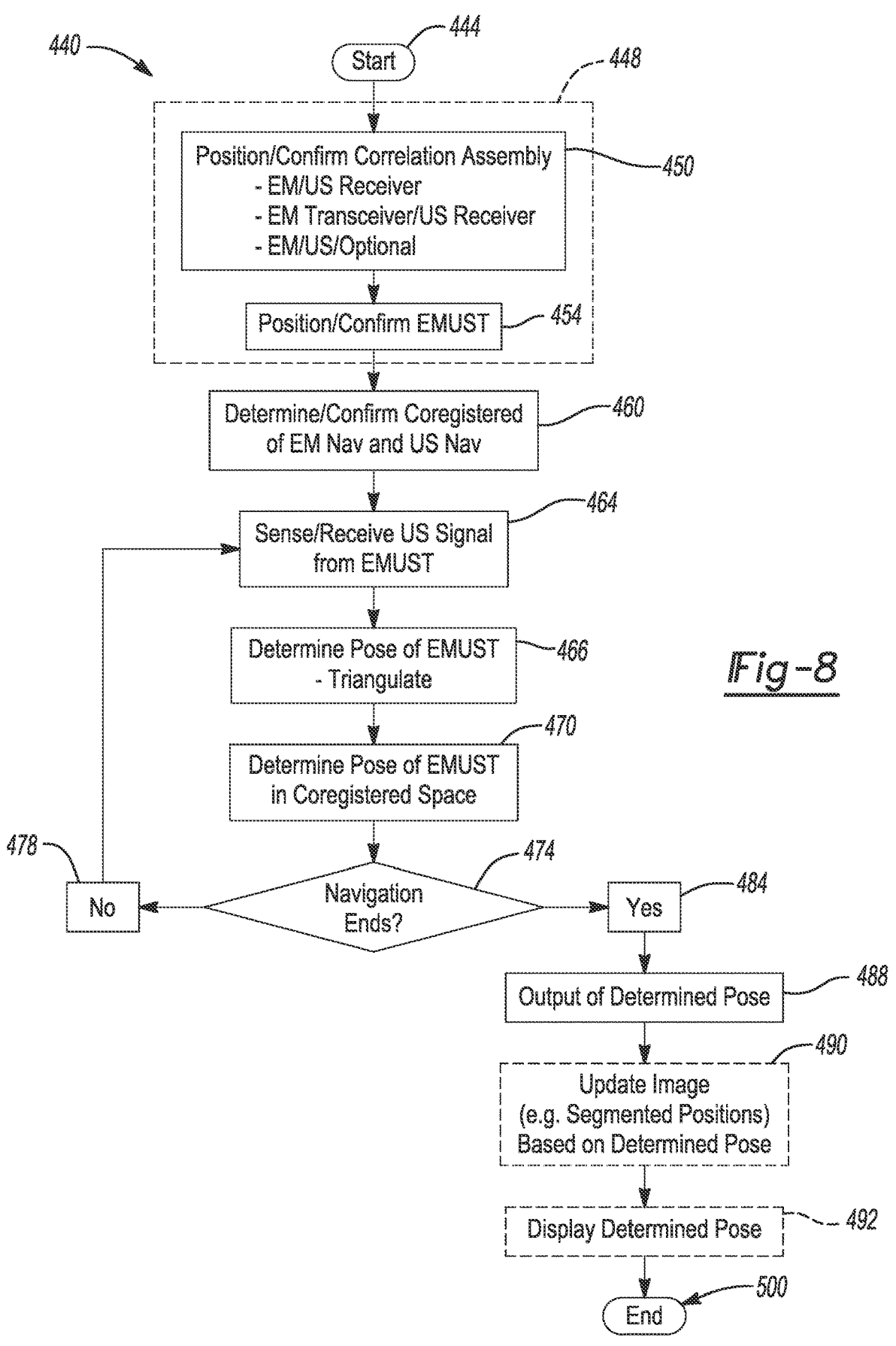
FIG. 8 is a flow chart of a navigation system using various tracking assembly.

Turning to FIG. 8, a method 440 may be used to assist in navigating a procedure, such as determining a pose of one or more of the portions of the subject 30 and/or the instrument 68. For example, the process 440 may begin and start block 444. A first sub-process 448 may include positioning and/or confirming placement of one or more of the EM/US receivers 180 in block 450. As discussed above, the EM/US receiver 180 may be registered to one another based upon the co-location or co-registration of both of the EM receiver portion 184 and the US receiver portion 186 and determining a relative pose between each provided EM/US receivers 180. The receiver 180 may also be referred to as a correlation assembly and allow for correlation or transformation between at least two navigation spaces, such as an EM navigation space and a US navigation space. Therefore, block 450 may include either or both of positioning or confirming a position of the EM/US receiver. This allows for confirming or determining a position of the EM/US receiver 180 in at least one of the tracking spaces, such as the EM tracking space or navigation space.

Further, the optional step 448 may include positioning or confirming a position of an EMUST 160 in block 454. The EMUST 160, as discussed above, may be positioned relative to the subject 30 in a selected manner. The EMUST 160 may be connected to a vertebrae, such as the vertebra 164. Accordingly, a plurality of EMUSTs may be connected to a plurality of vertebrae of the spine 166, such as one EMUST connected to each of a vertebra of the spine 166. Again the positioning or confirming of positioning of the EMUST may allow for the process 440 to allow for determining a pose of one or more portions of the subject 30 relative to other portions, such as the instrument 68 and/or the EM/US receivers 180. This may further be used to update, such as in real time, an image of portions that relate to the portions to which the EMUSTs 160 are associated, such as one or more segmented vertebrae.

The process 440 includes confirming or determining a co-registration of an EM navigation and US navigation in block 460. The co-registration may occur by determining a position of both the EM receiver 184 and the US receiver 186. For example, the two receivers may not be fixedly connected to one another prior to positioning relative to the subject 30. Alternatively, a tracked or determining of a position of both the EM receiver 184 and the US receiver 186 of the EM/US receiver 180 may be performed in the navigation space, such as with the localizer 94 and/or other receivers. This allows at least one point (also referred to as a registration point) to be known in at least the two navigation spaces, such as the EM and US navigation space. This allows for a transformation between the two navigation spaces.

Further, in various embodiments, each of the US receivers 186 may operate with each of the EMUST 160 to define a navigation space in the US tracking system or tracking space. Therefore, being co-registered to the EM navigation space may allow for registration to other spaces, such as the image space 180. As discussed above, the EM navigation system including the EM localizer 94 may be registered to the image space 108. Therefore, co-registering the US tracking system with the EM tracking system allows the US tracking system to also be registered to the image space 108. Also, the EM and US spaces may be registered to the image space by intraoperative imaging, such as imaging and identifying portions with a tracking device associated therewith.

An US signal may be emitted from a selected transmitter, such as an EMUST in block 464. The US signal may be in response to a transmitted EM signal. For example, as illustrated in FIG. 4, a plurality of the EMUST 160 may be included relative to the subject 30. Each may be positioned on one or more of the vertebrae 164. In block 464 a first US signal may be emitted by the EMUST_1 which may be any appropriate one of the EMUST 160. The signal may be sensed at one or more of the US receivers 186 at one or more of the EM/US receiver assemblies 180, such as the EM/US receiver of 180a and the EM/US receiver 180b.

A determination of at least one degree of freedom of the pose of the EMUST_1 be made in block 466. The determination, such as of the pose, may be based upon a triangulation of the received signal from the EMUST_1. As illustrated in FIG. 4, the EMUST 160 may transmit a signal that is received by the two EM/US receivers 180a, 180b. The triangulation may include a determination of the two distances, 220, 224. The determination of a pose that EMUST_1 may be made relative to the two EM/US receivers 180a, 180b.

Once the pose of the EMUST is determined, such as by triangulation in block 466, the pose of the EMUST may be determined in the co-registered space in block 470. As discussed above, the determination of the pose the EMUST and the co-registered space may be based upon a translation or transformation map between the two registration or navigation spaces, such as the EM navigation space and the US navigation space. Therefore, once the EMUST is determined in one space the pose may be determined in the co-registered space in block 470, such as with the transformation map.

A determination of whether navigation ends in block 474 may be made. If navigation is not ended, a NO path 478 may be followed to continue sensing receiving an US signal from EMUST'S. As discussed above, the various portions of the subject may have EMUSTs connected therewith. Therefore all or a selected number may have a pose determined in a selected navigation space, such as the US navigation space or the EM navigation space. The process 440 may iterate to determine a pose of all or selected number of EMUST'S or portions in a selected space, such as the US tracking space or the EM tracking space.

If navigation has ended a YES path 484 may be followed. In following the YES path in 484 an output of the determined to pose may be made in block 488. Outputting the determined pose may include outputting the determined pose in one or more of the navigation spaces, as determined above. Further the outputting may include storing one pose of one of the EMUSTs and waiting further poses to be determined due to the iterations of the processes 440. Nevertheless, the output of the determined pose may allow for the determined pose of one or more portions of the subject having the EMUST associated therewith to be determined and evaluated.

For example, the determined pose may be output and displayed in block 492. In displaying the outputted determined pose in block 492 the image data 108 may illustrate one or more portions of the subject and the related determined pose. As discussed above the instrument 68 may be moved relative to the subject 30. The movement of the instrument 68 relative to the subject may cause movement of one or more portions of the subject, such as one or more of the vertebrae relative to one another in the spine 166. Therefore the pose of the instrument may be tracked with the selected tracking system, such as the EM tracking system. The pose of one or more of the vertebrae of the spine 166 may be tracked with the EMUST associated therewith. For example, an exemplary portion of the image 108 may be updated, such as in real time. The image 108 may be segmented, according to known techniques. The segmentation may be of the vertebrae. An EMUST may be associated with a vertebra of the subject and at least one of the segmentation image portions. Thus, the image may be updated (e.g., in real time) due to the tracking of the EMUST in block 490.

The process 440 may allow for ensuring an updated and accurate (e.g., real time), display of an image of the subject 30. As noted above, the EMUST 160 may be connected with one or more portions of the subject 30, such as a vertebrae 164. Due to the known or fixed determination of the pose of the EMUST relative to the vertebrae 164, an image of the vertebrae may be updated with the current (e.g., tracked) pose thereof. For example, image data of the subject may be segmented using appropriate known segmentation techniques. The segmented portion may be associated with one or more of the EMUST 160. Therefore, determining a pose of the EMUST to may be used to determine a pose of the segmented portion of the image. The image of the subject, including the subject portions such as the vertebra 164 may, therefore, be updated in an image in block 490. The updated image may include positioning or displaying a real time pose of the segmented portion or other appropriate portion of the image based on the determined pose of the EMUST that is determined block 488.

The image may be updated, such as due to the co-registration of the EM navigation space and the US navigation space, such as with the EM/US receiver is 180, the pose of the portions of the subject may be displayed relative to the tracked pose of the instrument 68. Therefore the display device 84 may display the image data 108 and the icon 68i with the selected portions of the subject in a new or updated pose relative to a current tracked pose and/or real time pose in the instrument 68. Therefore, the displayed image may be displayed in substantially real time even if portions of the subject 30 have moved following the capture of selected image data. The image 108 may be updated by segmentation and movement of the segmented portions of the image, graphical representations of portions of the image in a current or real time pose, or other appropriate displays.

Regardless, determining the pose of selected portions may be made in output in block 488. The process 440 may then end in block 500. Ending the process in block 500 may include any appropriate procedures, such as completing a procedure of a subject, closing a portion of the subject, or the like.

As discussed above, various assemblies may be provided relative to the subject to allow for co-registration or co-relation of various navigational spaces. The co-relation assembly may be provided in various manners to assist in receiving or transmitting signals or fields and generating a signal based thereon to allow for the navigation assembly, including the navigation system 26, to correlate or co-register at least two navigation spaces or systems. The correlation assemblies, according to various embodiments, may include the EMUST 160 discussed above. The EMUST may generate a sound or ultrasound signal based on and/or due to an applied field that may be a frequency or time varying field. The field may be a magnetic field which may include an electromagnetic field. Without being bound by the theory, and with reference to FIG. 9, a system may include an EMUST that has at least a portion that varies in size or a selected dimension based upon an applied magnetic field.

As illustrated in FIG. 9, two axes include a field strength axis 540 and a dimension or change dimension axis 544 that intersect at an origin 548. The field strength axis 540 may illustrate a magnetic field H. The dimension axis 544 may illustrate a ratio of a change in dimension over a resting dimension. The origin 548 may illustrate when substantially no field is being applied and a material is at a resting dimension.

A dimension of the material (e.g., of the EMUST) is illustrated as line 552 representative relative to the two axes 540, 544. The material is illustrated as the line 552 and may have a change in a dimension, such as a length, width, or the like based upon an applied field. As the field value increases, the change in the dimension of the material (represented by line 552) may change in value as illustrated relative to the axis 544. A field may have a change in value 556 between a minimum value 558 and a maximum value 560. Between these two values of the field, as illustrated on the field axis 540, the material may have a selected or known dimensional change 564.

The amount of change may be known, or predetermined, and may be based upon a material or a material construction. Further, the material may be included in a selected construct, such as in the EMUST as illustrated above. According to various embodiments a selected item, such as a permanent magnet, may apply a biasing field 568 (Hb). The biasing field may ensure that the material, as illustrated by line 552, is at some set dimension that is not the resting dimension. The biasing field may be applied externally to the EMUST such that it is not required to include or contain a permanent magnet. Therefore, the varying field in the value of 556 may allow for a maximum or selected dimensional change of the material in more than one direction based on a varying field. By applying a varying field relative to the biased field value 568 the material may oscillate or vibrate.

As illustrated in FIG. 9, for example, the dimension change 564 may have an increasing dimension change portion 564i and a decreasing dimension value 564d relative to the bias value 568. Thus, applying the varying field may cause the material to increase and decrease in a selected dimension. Done at a selected rate this may cause the material to vibrate at a selected rate. Briefly, causing the material to vibrate at a selected rate may cause the material to vibrate at an ultrasonic rate and, therefore, transmit an ultrasonic signal that may be received at a selected US receiver.

Turning in reference to FIG. 10, the material having a possible change in dimension is illustrated by line 552 and may include a selective magnetostrictive material 580. The magnetostrictive material 580 may be any appropriate material, such as an elastic material having a magnetic portion (e.g., magnetic particle) therein. Further, various materials, such as alloys, may have magnetic resistive properties that will change dimension when a magnetic field is applied. Magnetostrictive materials may include metal or metal alloys such as Terfenol-D, Galfenol, Alfer, cobalt ferrite, and/or Metglas alloys such as 2605SC or other appropriate materials or combinations thereof.

As also discussed above, a magnetic field may be applied as a biasing magnetic field. Therefore, a biasing magnet or material 584 may be incorporated into a selected item, such as in EMUST 590. As noted above, the biasing field may be applied externally to the EMUST such that it is not required to include or contain a permanent magnet. The EMUST 590 may be incorporated into the EMUST 160, as discussed above. It will be understood that the various examples may be provided, as discussed herein, it may be selected for various applications. Therefore, the EMUST 590 may have magnetostrictive 580 that may have included therewith, such as within a center mass of the magnetostrictive material, a biasing magnet 584.

According to various embodiments, the EMUST 590 may have a selected dimension, such as a dimension 594. The dimension 594 may be any dimension of the EMUST 590, such as a length thereof. The dimension 594, however, may be the dimension that changes over time as a varying magnetic field is applied to the magnetostrictive material 580. Accordingly, the dimension 594 may change from a biased dimension and/or resting dimension as the magnetic field is applied in a varying manner, as illustrated in FIG. 9.

With continuing reference to FIG. 10, an EMUST 600 may also be provided. The EMUST 600 may include the magnetostrictive material 580 and a biasing magnet 584. The EMUST 600, however, may also include an elastic coating or housing 640. The elastic housing 640 may vary with the magnetostrictive material 580. The EMUST 600 may include a dimension 608. The dimension 608 may vary over time when the field is applied to the EMUST 600. The elastic coating or housing 640 may move with the magnetostrictive material 580 as the field varies.

The EMUST 600 may transmit a signal, such as directly to a subject. In various embodiments, as illustrated above, the EMUST 600 may be attached to the vertebra 164. When the EMUST changes dimensions or vibrates, the signal may be transmitted through the subject 30, such as through the tissue of the subject 30. Further, a vibration may be directly sensed and it may be amplified, such as by vibrating the vertebrae 164.

With the continuing reference to FIG. 10 an EMUST 620 is illustrated. The EMUST 620 may again include the magnetostrictive material 580 and the biasing magnet 584. The EMUST 620, however, may include an inelastic or hard shell 624. The shell or housing 624 may be a substantially rigid shell that does not change dimension with the magnetostrictive material 580. Therefore, the shell 624 may have a dimension 628. The magnetostrictive material 580 may also have the dimension 628 at a resting or bias time. However, the magnetostrictive material may change dimensions relative to the shell 624 as the field is applied, as illustrated in FIG. 9. The magnetostrictive material may be fixed to the shell 624, in at least one portion and/or may be free floating within the shell 624. Therefore, as the magnetostrictive material changes dimension, it may engage or hit the shell 624. In changing shape or hitting the shell 624 the magnetostrictive material may, therefore, transmit a sound signal or selected sound signal.

As discussed above, the field H may be applied in any appropriate manner. The permanent or biasing magnet 584 may apply a selected or fixed field relative to the magnetostrictive material 580, according to various embodiments. The varying field may be emitted by selected portions such as the localizer 94 or other appropriate emitting portions. According to various embodiments, including those discussed above, fields may be emitted that are sensed or applied to the magnetostrictive material. Based upon the varying field the magnetostrictive material may change dimensions, as discussed above. Therefore, the EMUSTS 590, 600, 620 may have their magnetostrictive material 580 that changes shape over time due to the changing magnetic field that may be emitted by various portions, such as the localizer 94 or other EM field emitting portions.

The frequency of the signal from the EMUST may vary based upon the frequency of the emitted field, such as from the localizer 94. Further, the US signal from the EMUST may change based upon the physical dimension or other characteristics of the EMUST. As illustrated in FIG. 10, the EMUST 590 includes the dimension 594, the EMUST 600 includes the dimension 608, and the EMUST 620 includes the dimension 628. Each of the three dimensions 594, 608, 628 may allow the respective EMUSTS to transmit known or specific signals. This may allow for the respective EMUSTS to be identified when a signal is received that is or relates to the known or predetermined frequency of the respective EMUST. Therefore, the EMUST activated with the selected EM field and the EMUST may emit a known signal that may be based upon various characteristics, such as the respective dimensions 594, 608, 628. As discussed above, the pose of the respective EMUSTS 590, 600, 620 may then be determined such as by triangulation to US receivers.

The EMUST, according to various embodiments, may be provided with various configurations, including those discussed above. The various configurations may include the EMUST 160 and/or the various embodiments or variations thereof as noted above. Various embodiments of the EMUST include those illustrated in FIG. 11. The EMUST as illustrated in FIG. 11 may change shape or vibrate according to various configurations.

For example, an EMUST 650 may be understood to be a single sided EMUST. The single sided EMUST may still be anisotropically shaped such that a signal that is measured at various relative locations may be distinguished from another to allow for determination of at least one degree of freedom. As discussed above, the EMUST 650 may include the magnetostrictive material 580. Further the EMUST 650 may include the biasing magnet 584. The magnetostrictive material may be in the biased configuration when no external field, such as from the localizer 94, is applied or experienced by the EMUST. Therefore, the EMUST may be in a biased or resting state 650'. The magnetostrictive material 580' also be in the biased or resting state 580.

As noted above, the field may be applied to the EMUST 650. For purposes of the following discussion the field may be a negative or a positive field. Accordingly, the field applied to the EMUST may be a negative field such that the magnetostrictive material includes a change in shape including that it moves in a first direction, such as the direction of arrow 654. The magnetostrictive material and the negative field configuration may be illustrated as the magnetostrictive material 580'. The EMUST may also have a negative field configuration 650". When a positive field is applied it the EMUST may be in a positive field EMUST configuration 650'''. The magnetostrictive material may also be in a positive field configuration 580". In this configuration the magnetostrictive material 580 may generally move in the direction of arrow 658.

Accordingly, relative to a selected axis 662 the magnetostrictive material 580 only moves in two directions depending upon the field being applied or experienced by the EMUST 650. In this single sided configuration the EMUST will generally only emit a single sided signal that may be sensed and received as the US signal. According to various embodiments the EMUST 650 may include a hard shell 668 and the magnetostrictive material 580 may contact the shell 668 when making the signal. According to various embodiments, however, the EMUST 650 may include an elastic shell or housing or no housing.

Nevertheless, the EMUST may be designed to move in only two directions, such as relative to the axis 662. Thus the EMUST 650 may understood to be a single sided EMUST. The signal emitted by the EMUST 650, and according to various embodiments, may have an amplitude of a selected value. Nevertheless the US signal would generally appear to generate from an origin and radiate in one direction from the origin. In other words, the single sided EMUST would signal towards one direction (i.e., one half volume, such as one half of a spherical volume) but the signal would spread out in the half volume defined by the single side. In various examples, there may be a leak behind that half volume (i.e., in the opposite direction of the signal direction).

In various embodiments, as illustrated in FIG. 12, a multiple sided (e.g., quadrupole) EMUST 680 is illustrated. The multiple sided EMUST may still be anisotropically shaped such that a signal that is measured at various relative locations may be distinguished from another to allow for determination of at least one degree of freedom. Again, the multiple sided EMUST 680 may include a magnetostrictive material 580 and the biasing magnet 584. Again the magnetostrictive material 580 may have a resting or biased state such as in the EMUST configuration 680'. When a negative field is applied, the magnetostrictive material may have a negative configuration 580' such as when the EMUST is in the negative configuration 680".

When the magnetostrictive material is the negative field it may move in at least two directions, such as expanding along an axis 688 in contracting toward the axis 688. Therefore, in the negative field state the magnetostrictive material 580' may move in two directions simultaneously. The two directions being perpendicular to and parallel with the axis 688.

In a reverse manner when a positive field is applied and the EMUST is in the positive field configuration 680", the magnetostrictive material 580" may also move in two directions, but opposite the negative field configuration. Therefore the magnetostrictive material 580 may compress along the axis 688 and expand away from the access 688. The two directions being perpendicular to and parallel with the axis 688.

In the multiple sided configuration the magnetostrictive material 580 may move in two directions simultaneously when experiencing varying fields. Thus, the EMUST 680 may emit a signal towards at least two directions, or more from an origin when experiencing the varying field.

The respective single or multiple sided configurations may be achieved by various constructions of the EMUST, selection of materials, or the like. For example the EMUST material may be substantially free moving within a housing or not include a restrictive housing to allow for more motion of the magnetostrictive material 580. The multiple sided configuration may also allow for additional information to be received at a US receiver given that the multiple direction signal that may be emitted by the multiple sided EMUST. The multiple direction signal relative to an origin or an identified origin of the EMUST provides varying signals and directionality to assist in determining orientation in addition to position of the EMUST. The signal, however, may have a lower amplitude given its greater diversity.

Nevertheless, the EMUST may be configured in various embodiments to emit a selected signal. As discussed above the shape in construction may allow for a selected frequency to be emitted by the EMUST based upon the parameters thereof. Further parameters may also include defining or forming the EMUST to be a single or multiple sided EMUST. The emitted signal may then be received by the US receiver and may be analyzed by the navigation system to determine a pose of the EMUST. As discussed above the pose of the EMUST may then be used to determine a pose of a selected portion of a subject or any appropriate portion to which the EMUST is connected.

Figure 13:
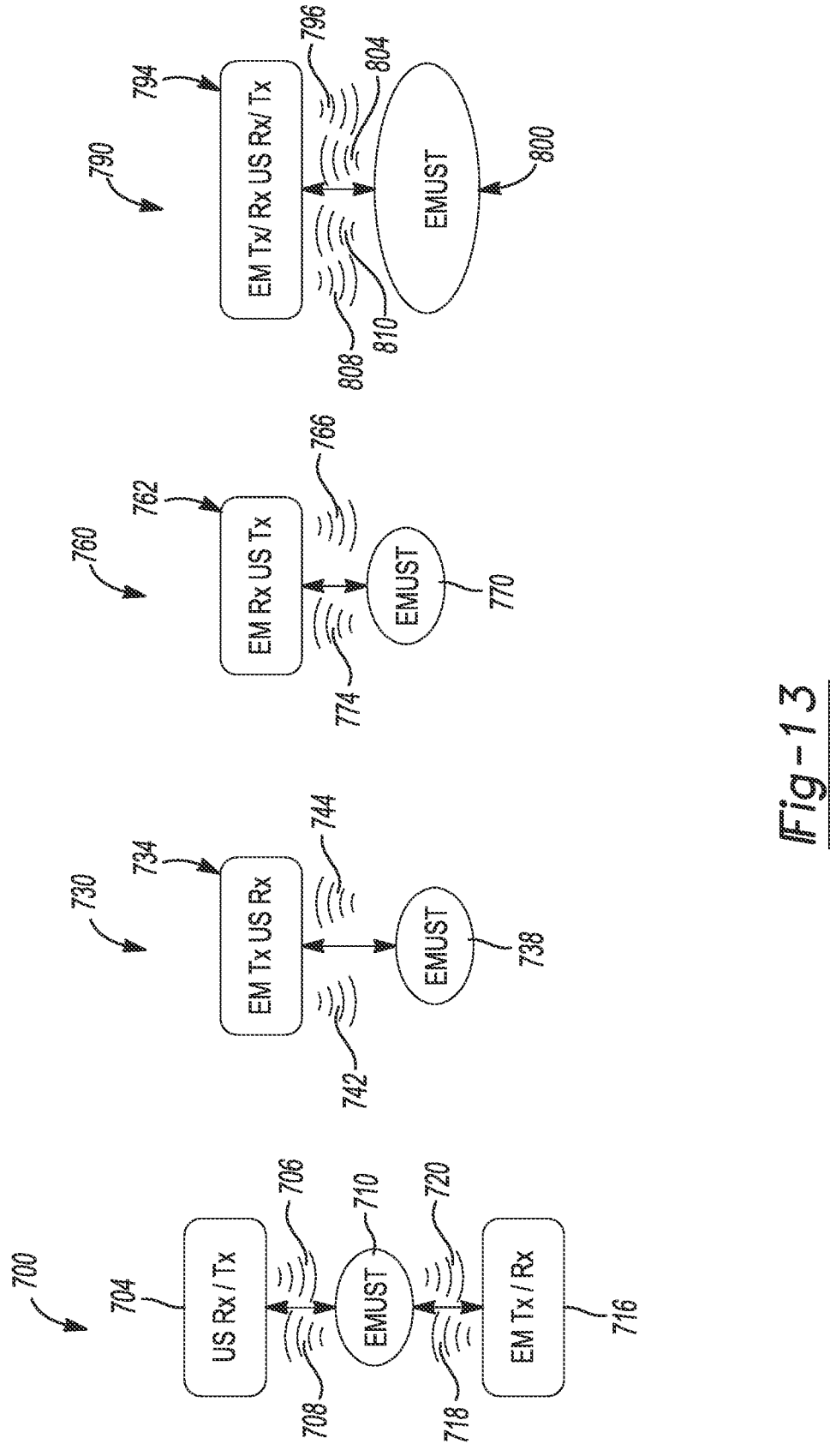
FIG. 13 is a schematic illustration of various communication schemes, according to various embodiments.

Turning in reference to FIG. 13, various configurations of communication (and related system portions) are illustrated. The EMUST may transmit or receive a signal in various portions and may also transmit or emit a signal. As illustrated above, the navigation system may include the localizer 94, an ultrasound receiver, and optical localizer and optical tracking device, and other appropriate configurations. The EMUST may be activated by a magnetic field, as also discussed above. Activation or affecting the EMUST with a magnetic field may cause it to vibrate and emit an ultrasonic signal and/or emit or generate a field. Similarly, the EMUST may also receive an ultrasound signal and emit a magnetic or electromagnetic field that may be sensed. Thus, the EMUST may be an US transducer and an EM transducer.

Therefore, as illustrated in FIG. 13, various configurations of a system may be provided that allow for co-relation or co-registration between a plurality of navigation spaces using a signal from or field generated by the EMUST and other related systems. For example, in a first exemplary configuration 700 an ultrasound receiver and transmitter 704 may emit an ultrasound signal 706 or receive an ultrasound signal 708. An EMUST 710 may receive an ultrasound signal and transmit an ultrasound signal. Further a EM transceiver 716 may emit a EM field 718 and receive an EM field 720. According to various embodiments, therefore, an EM navigation space may be co-related to a US navigation space and/or allow for transmission there between by having an EM transceiver 716 emit the EM field 718 that is received at the EMUST 710 and the EMUST 710 may transduce the EM field to an ultrasound signal 708 that is received at the US receiver. In a reverse manner, the US transceiver 704 may emit the US signal 706 that is received and sensed at the EMUST 710. The EMUST 710 may transduce the US signal to an EM field 720 that is sensed at the EM receiver 716. Thus, a transformation between the EM system and US system may be made with the EMUST as exemplary illustrated in the systems 700.

Various other systems may also be used. For example, an exemplary system 730 may include a combination EM transmitter and US receiver 734, as illustrated in a similar system above. An EMUST 738 may be provided according to various embodiments, as discussed above. As illustrated in the system 730, the combination EM transmitter and US receiver 734 may emit an EM signal that is transduced by the EMUST 738 to then emit an US signal 744. Therefore, a co-relation or co-registration may occur between the US and EM system by the configuration 730.

A further exemplary configuration 760 may include a combination EM and US system that includes an EM receiver and the US transmitter. In the exemplary system 760, the US transmitter may transmit an US signal 766 that is received at the EMUST 770. The EMUST 770 may then transduce the US signal and emit an EM field 774 that is received at the combination EM receiver and USB transmitter 762.

In a further exemplary embodiment, a system 790 may include a combination EM transceiver and US transceiver. The combination transceiver 794 may emit an US signal 796 that is received at the EMUST 800. The EMUST 800 may then transduce the US signal to emit an EM field 804. The EM field may be received at the EM transceiver combination system 794. In an alternative or additional operation the combination transceiver 794 may emit an EM field 808 that is received at the EMUST 800. The EMUST may transduce the EM field and emit the US signal 810. The US signal 810 may then be received at the combination transceiver 794. In this configuration, the system 790 may emit and receive both EM and US signals. The operation thereof may be selected for various purposes, such as for selected tracking portions, positioning of interfering items, or other selective limitations.

Nevertheless, the various system configurations 700, 730, 760, and 790 are exemplary embodiments for operation of a system including an EMUST, occurring to various embodiments. The system may include a combination of various portions illustrated above, as understood by one skilled in the art. The various configurations or combinations thereof allow for correlated portions, including those various embodiments discussed above an exemplary illustrated in the schematic drawing in FIG. 13. Thus, the EMUST may allow for operation or correlation between two or more navigation spaces or systems, such as an EM navigation system and a US navigation system.

The various systems, discussed above may be provided according to various embodiments. For example the EMUST 160 may be provided with the subject 30. The EMUST may include various features that may be identified separately by various navigation systems, such as an ultrasound navigation system or an electromagnetic navigation system. According to various embodiments the EMUST may be provided attached to the subject and/or associated with other portions, such as the instrument.

As illustrated in FIG. 14, an instrument assembly 800 is illustrated. The instrument assembly 800 may include a tracking device (also referred to as a tracking device assembly) 804. The tracking device 804 may include or be an EMUST, according to various embodiments. As discussed above and herein the EMUST 804 may both receive and emit EM fields and receive and emit ultrasound signals. Therefore the EMUST 804 may be an EM transducer and an ultrasound transducer. The EMUST 804 may be a tracking device or provided as a tracking device with an instrument 806. The instrument 806 may be provided as a movable instrument, such as the instrument 68 as discussed above. Further the instrument 806 may be a portion that is provided with the subject, such as positioned within tissue and/or connected to heart tissue in the subject. The tracking device 804 may be associated with the instrument 806 in an appropriate manner, such as wound around or provided around an exterior surface 808 of the instrument 806. The instrument 806 may further define an internal cavity or bore 812 that may have an internal wall 814. The instrument 806, however, may be provided in any appropriate manner and the portion illustrated in FIG. 4 may simply be a portion of an instrument, such as a distal tip. Further the instrument 806 may be an entire instrument that is positioned in the subject for various purposes, including those discussed above and further herein.

The tracking device 804 may include various portions including a coil portion 820. The coil portion 820 may include a conductive member that is wrapped around the external surface 808. The coil 820 may include a metallic or conductive wire of an appropriate material. The coil 820 may be formed of a wire or selected material that may include a metal or metal alloy, conductive polymer, or other appropriate material. The coil 820 may, however, be provided in a manner as a generally known or understood in the art, including those discussed above. The coil 820 may operate with the navigation system, such as the EM navigation system, including the localizer 94 or any appropriate localizer that may emit a field. The coil 820 may sense the field and have a voltage or current induced therein. As noted above the induced voltage or current may be used to generate a signal or send a signal to the navigation system 26 to allow for a determination of a pose of the instrument 806 in a navigation space.

Figure 14A:
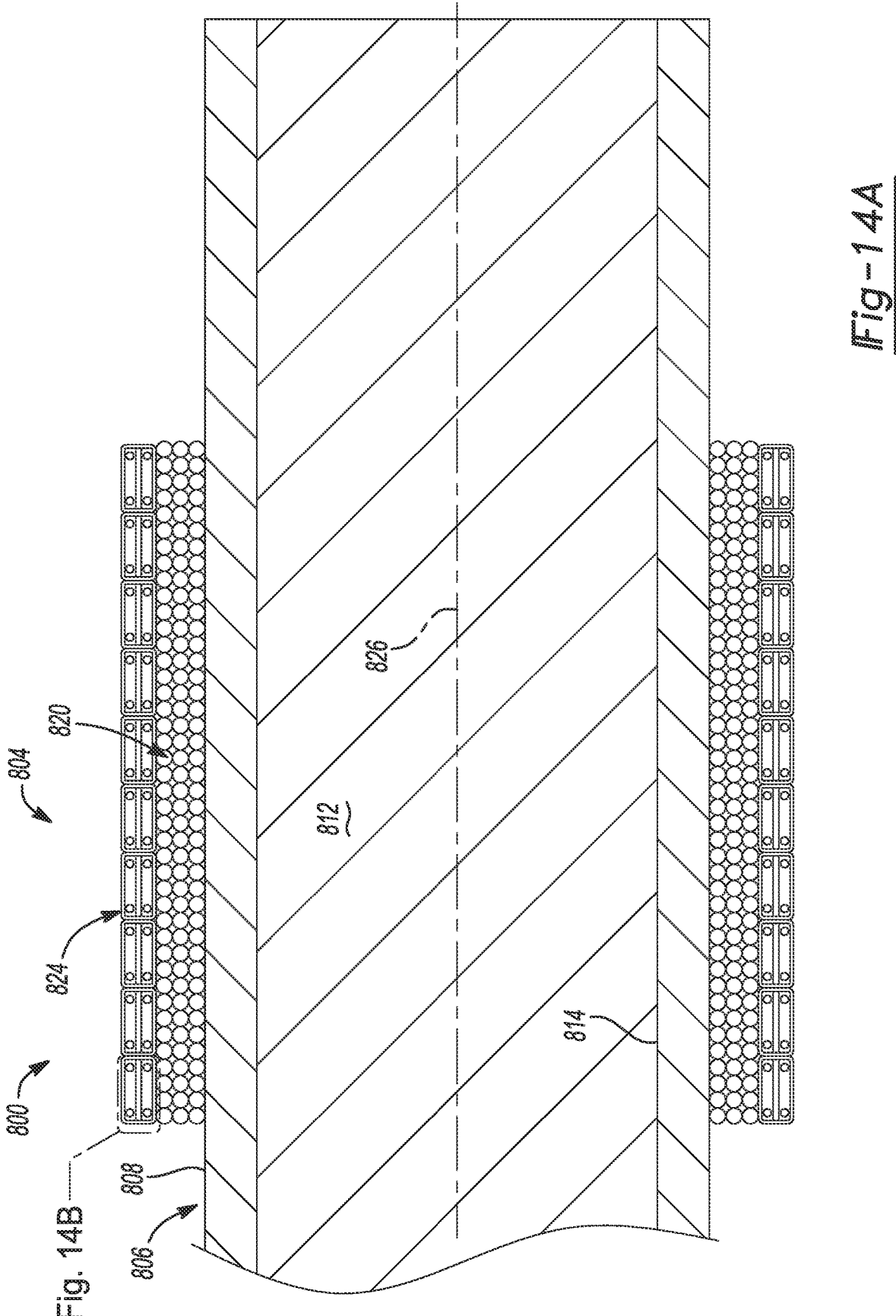
FIG. 14A is a schematic illustration of a co-wound tracking assembly, according to various embodiments.

The tracking device 804 may also include a composite piezoelectric or composite member 824. The composite piezoelectric member may be an appropriate member that include various portions. For example, the composite piezoelectric member 824 may be provided as an elongated member that is also wrapped or co-wrapped around the instrument 806. Accordingly, the instrument 806 may have a central axis 826 around which both of the composite piezoelectric member 824 and the coil 820 are wound. As illustrated in FIG. 14A, the coil 820 and the composite piezoelectric 824 may be co-wound such that the coil 820 is between the piezoelectric composite member 824 and the surfacing 108. It is understood, however, that the reverse may be formed such that the composite piezoelectric member 824 is between the coil 820 and the surface 808.

Figures 14B, 15:
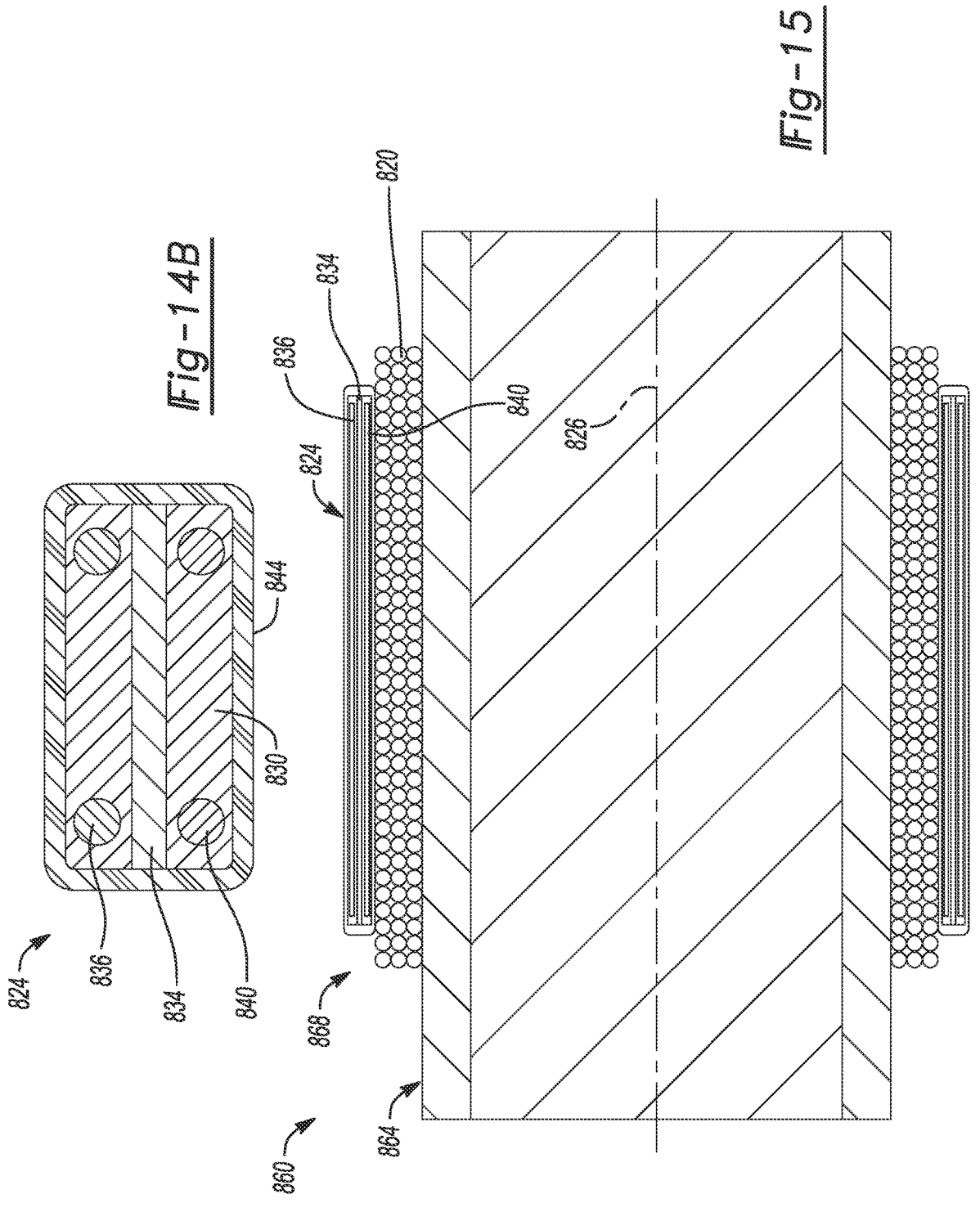
FIG. 14B is a schematic illustration of a composite piezoelectric member, according to various embodiments.
FIG. 15 is a schematic illustration of the co-wound tracking assembly, according to various embodiments.

The composite piezoelectric member 824 may have a selected construction. For example, as illustrated in FIG. 14B, a support material 830 may be included. The support material may be used to encase or pot selected materials, such as piezoelectric material 834 and one or more conductors such as a first conductor 836 and a second or return conductor 840. In various embodiments, the support material may be carbon loaded polyethylene. The composite piezoelectric fiber coil 824 may be encased in a selected housing or cover 844. According to various embodiments, the composite piezoelectric material or member 824 may be flexible such that it may be wound around the instrument 806 and the housing 844, therefore, is similarly flexible. The housing 844 may be provided as a fiber, such as a polyester or nylon fiber material that allows for the composite member 824 to be manipulated and formed into a selected configuration or shape. As is generally understood in the art, a piezoelectric material may be altered, for example to change shape as noted above, when an electric field or voltage is applied to the piezoelectric material. Similarly, when a physical force is applied or exhibited to the piezoelectric material, a voltage may be induced therein or related to conductive material. Accordingly, the conductors 836, 840 may be used to transmit a voltage to the composite member 824. The piezoelectric material 834 may then change shape or be urged to change shape based upon the applied voltage. Similarly, a force applied to the piezoelectric material 834 may induce or generate a voltage that may be transmitted or sensed at the conductors 836, 840. Thus, the composite member 824 may be used to transmit or sense a force, such as one that is applied by a pressure wave, such as in an ultrasound frequency. Similarly, the induced field may be generated or sensed by the voltage on the conductors 836, 840. Therefore, the composite member 824 may transduce in the US and EM tracking systems. The composite member 824 may be used to co-register US and EM navigation spaces and may be used to sense an US signal, as discussed further herein. Exemplary composite materials that may be useful as the composite member 824 include those disclosed in Yan, W., Noel, G., Loke, G. et al. Single fibre enables acoustic fabrics via nanometre-scale vibrations. Nature 603, 616-623 (March 2022). https://doi.org/10.1038/s41586-022-04476-9.

Turning to reference to FIG. 15, an instrument assembly 860 may include an instrument portion 864. This instrument may be similar to the instrument 806 as illustrated in FIG. 14A. The instrument assembly 816 may also include a tracking device portion 868. The tracking device portion 868 may include the coil 820, as discussed above. The tracking assembly 868 may further include the composite member 824. The instrument assembly 860 may be similar to the instrument assembly 800, as discussed above, including the coil 820 that is wrapped around the axis 826 of the instrument 864, such as an outer surface thereof. The composite member 824, however, may position substantially along or parallel with the axis 826. Therefore, rather than being wrapped around to the axis 826, the conductor 836, 840 may be parallel with the axis 826. Similarly, the piezoelectric material 834 may also be substantially parallel therewith. Thus, the composite assembly tracking portion 868 may be positioned on the instrument 864 in a selected manner.

Figure 16:
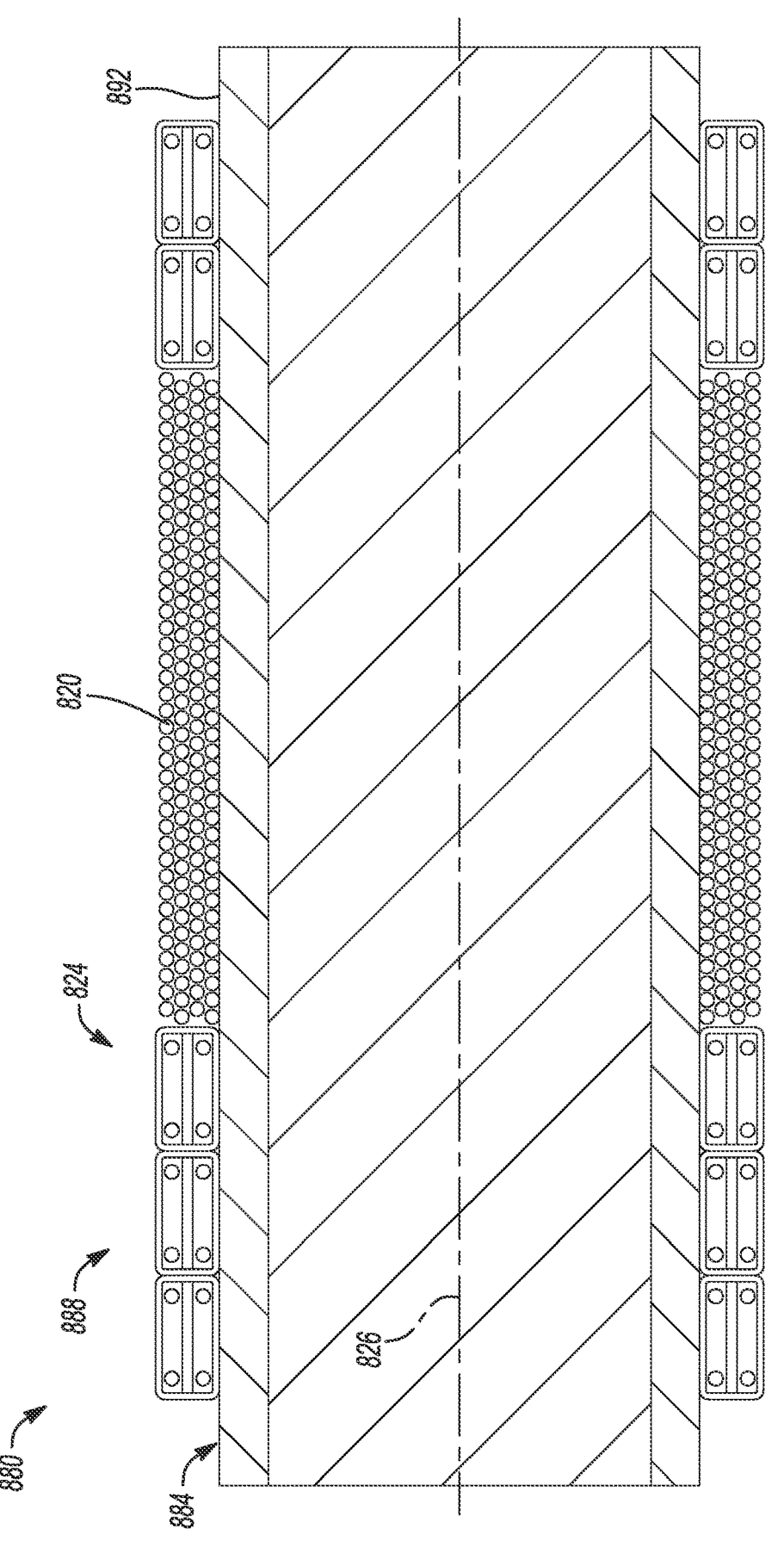
FIG. 16 is a schematic illustration of a co-wound tracking device assembly.

Turning to reference to FIG. 16, an instrument assembly 880 illustrated. The instrument assembly 880 may include an instrument 884 similar to the instrument as discussed above including the instrument 806. The instrument assembly 880 may include a tracking assembly 888 including the coil 820 and the composite member 824. The coil 820 may be wrapped around a central axis 826 of the instrument 884. Similarly the composite material 824 may be wrapped around the central axis 826 of the instrument 884.

As illustrated in FIG. 16 both of the composite material 824 and the coil 820 may be positioned on an exterior surface 892 of the instrument 884. Thus, the overall width of the instrument assembly 888 may be minimized to be no greater than a width of either one of the coil 820 or the composite member 824. Thus, rather than being co-round at the same position, as illustrated in FIG. 14A, the coil 820 and the composite member 824 may be positioned adjacent to one another along the axis 826. It is understood that the composite material 824 may be positioned on either side or both sides (as is illustrated in FIG. 16) of the coil 824.

Accordingly, as illustrated above, a plurality of configurations may be provided to include a composite or dual tracking portion. The coil 820 may be provided to interact directly and only with the EM navigation system in space. The composite material 824 may be provided to interact with an ultrasound and an EM system. The composite member 824 may be used as an EMUST, as discussed above. Nevertheless, having the co-wound assembly may allow for correction or accuracy between a US navigation system and space and an ultrasound navigation system and space.

According to various embodiments, at least one of the first conductor 836 or the second conductor 840 of the composite member 824 may be operated as the coil 820. Thus, a separate coil 820 is not required and the composite material may operate as both an EM tracking device and an US tracking device. The composite material 824 may be the only tracking device associated with a selected item, such as the instrument or any appropriate member or portion as discussed above. The composite material may sense a signal that is either an EM field with the first conductor 836 or the second conductor 840 and the US signal with the piezoelectric material. The related signals may then be transferred to the navigation system 20 for determining the pose of the tracking device which may include only the composite member 824.

Figure 17:
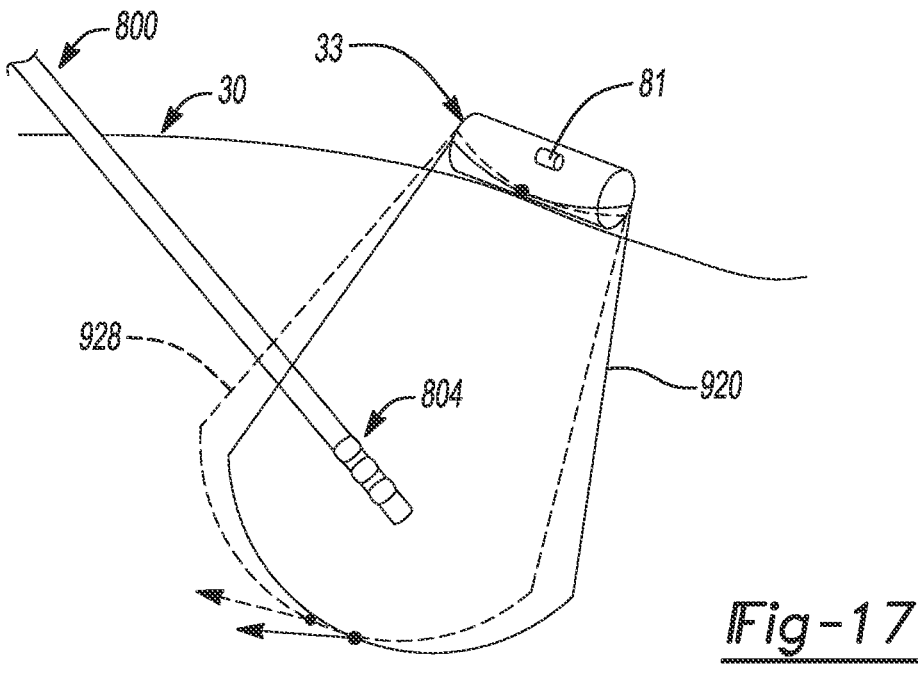
FIG. 17 is a schematic illustration of an ultrasound imaging system and an instrument having a compound tracking device associated therewith, according to various embodiments.
Figure 18:
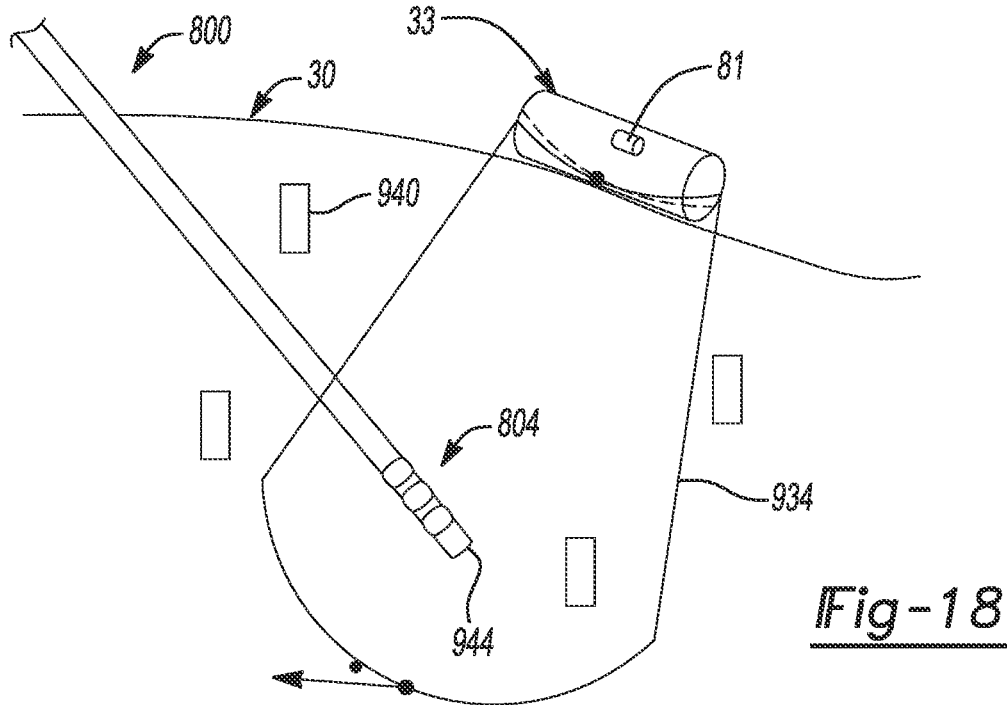
FIG. 18 is a schematic illustration of a tracked ultrasound imaging device and a tracked instrument with a co-wound tracking device, according to various embodiment.

Turning in reference to FIG. 17 and FIG. 18 an instrument, such as the instrument assembly 800 may be positioned relative to the subject 30, as discussed above. While the instrument 800 is discussed here, it is understood that the instrument 800 is merely exemplary of various embodiments including those discussed above, and is understood by one skilled in the art. The instrument 800 may have the co-wound or co-position tracking portion 804, as discussed above. Further, it is illustrated in FIG. 17, a ultrasound probe plane 920 may be emitted by an ultrasound probe, such as the ultrasound probe 33 as discussed above. The ultrasound probe 33 may be tracked with a select tracking device, such as the tracking device 81. The tracking device 81 may be an EM tracking device. Therefore, the EM navigation system may be operated to track the position of the US probe 33. As discussed above the position of the ultrasound imaging plane may be determined by the navigation system, and may be used for relation tracking to the instrument 800. As illustrated in FIG. 17, however, the imaging plane 920 may be offset from the navigated plane 928. The difference between the actual imaging plane 920 and the navigated imaging plane position 928 may be caused from various issues such as an erroneous calibration of the ultrasound probe 31, distortion in navigation field, or other various inaccuracies.

Nevertheless, the combination or co-wound tracking device 804 may include the composite member 824 that may sense the ultrasound signal from the US probe 33. Similarly, the coil 820 may sense the navigation field for determining a pose of the instrument 800 in the navigation space of the EM navigation system. When the US probe is used to generate an image, such as the image 108 and the pose of the instrument 800 is determined with a tracking device, such as the coil 820 the two may be displayed relative to one another based upon the navigated pose of both. However, if an inaccuracy occurs, the displayed pose of the instrument 800 may not be accurate relative to the image plane 920 of the US probe 33. Even if the tracking device 81 is associated with the US probe 33 and is used simultaneously. Accordingly, the co-wound tracking device 804 may allow for a correction of the navigated pose of the instrument 800 relative to the navigated plane 928. By sensing the ultrasound signal from the US probe 33. The co-wound tracking device 804 may be used to determine a pose of the actual imaging plane 920 relative to the tracking device 804 and allow for correction of the displayed image on the display device, such as the display device 84 to illustrate inappropriate pose of the image 108 and a graphical representation, such as the graphical representation 68i.

With reference to FIG. 18, the displayed image 108 and graphic representation 68i may be corrected due to a correction determined with the combination tracking device 804. A corrected imaging plane and a navigated imaging plane 934 may then be determined. The displayed image 108 may include a corrected position of the portion being imaged of the subject 30. Similarly co-wound instrument portions 940 may be positioned within the subject 30. The co-wound imaging portions may be positioned relative to the subject, such as on a surface thereof, or positioned near a therapy position, such as at or near distal end of 944 of the instrument 800. The co-wound portions 940 may be provided in any appropriate number relative to the subject 30. Nevertheless as the co-wound portions 940 may include both of the compound member 824 and the coil 820 they may be used to sense both an ultrasound signal from the US probe, or other appropriate ultrasound navigation system, in the EM field from the EM navigation system. Therefore, the co-wound portion 940 may be used alternatively or additionally to the tracking assembly 804 of the instrument 800. Regardless, the actual imaging plane 920 and the navigated position of the imaging plane 928 may be corrected or co-localized to ensure that to the navigated or displayed pose of the instrument 800 relative to the actual imaging plane 920 is as accurate as possible and, therefore, allow for proper illustration of the graphical representation 68i of the instrument, such as the instrument 800 on the display device.

According to various embodiments, the composite member 824 of tracker 804 may transmit US signals. Thus, as noted and illustrated above, the tracking device with the composite member may be operable to be tracked with a US system based on emitted US signals due to sensed or received EM fields. As an example, the navigation system may transmit, such as with the EM localizer 94, one or more time varying EM fields. These fields may induce a time varying voltages across conductive members 836 and 840 or across coil 820 which may be connected to conductive members 836 and 840. These time varying voltages may induce vibrations in the piezoelectric material 834. These vibrations may transmit sonic or ultrasonic signals from composite member 824 of tracker 804. These signals may be received by the US probe 33. The system may coordinate the EM and US subsystems so that the EM field and sonic or ultrasonic signal from composite member 824 of tracker 804 are frequency separated from US signals transmitted from US probe 33 and synchronized to be received with US probe 33. As such, the composite member 824 of tracker 804 may be localized in US space inside or outside of the US probe fan 920. And since the composite member 824 or the coil 820 or both of tracker 804 may be localized in EM space we may co-register the EM and US spaces with one or more trackers 804.

EXAMPLES

1. A tracking system, comprising: a tracking assembly including: a composite member having at least a piezoelectric material, and a conductive coil; wherein the tracking assembly is configured to be associated with a tracked object.

2. The system of claim 1, wherein the conductive coil is formed of a coil of conductive material; wherein the coil of conductive material is separate from the composite member.

3. The system of claim 1, wherein the conductive coil is formed of a coil of conductive material; wherein the coil of conductive material is integral with the composite member.

4. The system of claim 1, wherein the composite member and the conductive coil are both wrapped around an axis of the tracked object.

5. The system of claim 4, wherein a first of the composite member or the conductive coil is wrapped over a second of the composite member or the conductive coil.

6. The system of claim 1, wherein the composite member is placed parallel to an axis of the tracked object.

7. The system of claim 1, wherein the composite member includes a conductor to at least one of (1) impose a first voltage on the piezoelectric material or (2) have a voltage induced therein based on a movement of the piezoelectric material.

8. The system of claim 7, wherein the composite member is configured to transduce an ultrasound signal; wherein (1) the ultrasound signal is sensed by the composite member and the composite member imposes the second voltage on the conductor or (2) the first voltage causes a physical change in the piezoelectric material that generates the ultrasound signal.

9. The system of claim 1, further comprising: an electromagnetic tracking system configured to track the tracking assembly; an ultrasound tracking system configured to track the tracking assembly; an ultrasound imaging device configured to emit an ultrasound imaging region; wherein a tracked pose of the tracked object relative to a tracked pose of the ultrasound imaging region is operable to be determined at least by one of the electromagnetic tracking system or the ultrasound tracking system based on tracking the tracking assembly.

10. The system of claim 1, further comprising: an ultrasound imaging device configured to emit an ultrasound imaging region and receive an ultrasound signal from the tracking assembly; an electromagnetic tracking system configured to track the ultrasound imaging device; wherein a tracked pose of the tracked object relative to a tracked pose of the ultrasound imaging region is operable to be determined at least by one of the electromagnetic tracking system or an ultrasound tracking system based on the received ultrasound signal from the tracking assembly.

11. A method to track an object, comprising: providing a tracking assembly including: a composite member having at least a piezoelectric material, and a conductive coil; configuring the tracking assembly to be associated with the object.

12. The method of claim 11, further comprising: forming the conductive coil of a coil of conductive material; and positioning the coil of conductive material separate from the composite member.

13. The method of claim 11, further comprising: forming the conductive coil of a coil of conductive material; and forming the coil of conductive material integral with the composite member.

14. The method of claim 11, further comprising: wrapping both the composite member and the conductive coil around an axis of the instrument.

15. The method of claim 13, further comprising: wrapping a first of the composite member or the conductive coil over a second of the composite member or the conductive coil.

16. The method of claim 11, further comprising: placing the composite member parallel to an axis of the instrument.

17. The method of claim 11, further comprising: providing the composite member with a conductor to at least one of (1) impose a first voltage on the piezoelectric material or (2) have a voltage induced therein based on a movement of the piezoelectric material.

18. The method of claim 16, further comprising: configuring the composite member to transduce an ultrasound signal including (1) sensing the second voltage imposed on the conductor by the composite member based on the ultrasound signal or (2) controlling a physical change in the piezoelectric material with the first voltage to generate the ultrasound signal.

19. The method of claim 11, further comprising: tracking the tracking assembly with an electromagnetic tracking system; tracking the tracking assembly with an ultrasound tracking system; operating an ultrasound imaging device to emit an ultrasound imaging region; and determining a pose of the object relative to a tracked pose of the ultrasound imaging region at least by one of the electromagnetic tracking system or the ultrasound tracking system based on tracking the tracking assembly.

20. The method of claim 11, further comprising: operating an ultrasound imaging device to emit an ultrasound imaging region and receive an ultrasound signal from the tracking assembly; tracking the ultrasound imaging device with an electromagnetic tracking system; determining a pose of the object relative to a tracked pose of the ultrasound imaging region at least by one of the electromagnetic tracking system or an ultrasound tracking system based on the received ultrasound signal from the tracking assembly.

1. A tracking system, comprising: a tracking assembly including: a composite member having at least a piezoelectric material, and a conductive coil; wherein the tracking assembly is configured to be associated with a tracked object.

2. The system of claim 1, wherein the conductive coil is formed of a coil of conductive material; wherein the coil of conductive material is at least one of (1) separate from the composite member or (2) integral with the composite member.

3. The system of claim 1 or 2, wherein the composite member and the conductive coil are both wrapped around an axis of the tracked object.

4. The system of claim 3, wherein a first of the composite member or the conductive coil is wrapped over a second of the composite member or the conductive coil.

5. The system of claim 1 or 2, wherein the composite member is placed parallel to an axis of the tracked object.

6. The system of claim 1 or 2, wherein the composite member includes a conductor to at least one of (1) impose a first voltage on the piezoelectric material or (2) have a voltage induced therein based on a movement of the piezoelectric material.

7. The system of claim 6, wherein the composite member is configured to transduce an ultrasound signal; wherein (1) the ultrasound signal is sensed by the composite member and the composite member imposes the second voltage on the conductor or (2) the first voltage causes a physical change in the piezoelectric material that generates the ultrasound signal.

8. The system of claim 1 or 2, further comprising: an electromagnetic tracking system configured to track the tracking assembly; an ultrasound tracking system configured to track the tracking assembly; an ultrasound imaging device configured to emit an ultrasound imaging region; wherein a tracked pose of the tracked object relative to a tracked pose of the ultrasound imaging region is operable to be determined at least by one of the electromagnetic tracking system or the ultrasound tracking system based on tracking the tracking assembly.

9. The system of claim 1 or 2, further comprising: an ultrasound imaging device configured to emit an ultrasound imaging region and receive an ultrasound signal from the tracking assembly; an electromagnetic tracking system configured to track the ultrasound imaging device; wherein a tracked pose of the tracked object relative to a tracked pose of the ultrasound imaging region is operable to be determined at least by one of the electromagnetic tracking system or an ultrasound tracking system based on the received ultrasound signal from the tracking assembly.

10. A method to track an object, comprising: providing a tracking assembly including: a composite member having at least a piezoelectric material, and a conductive coil; configuring the tracking assembly to be associated with the object.

11. The method of claim 10, further comprising: forming the conductive coil of a coil of conductive material; and positioning the coil of conductive material at least one of (1) separate from the composite member or (2) integral with the composite member.

12. The method of claim 10 or 11, further comprising: wrapping both the composite member and the conductive coil around an axis of the instrument.

13. The method of claim 12, further comprising: wrapping a first of the composite member or the conductive coil over a second of the composite member or the conductive coil.

14. The method of claim 10 or 11, further comprising: placing the composite member parallel to an axis of the instrument.

15. The method of claim 10 or 11, further comprising: providing the composite member with a conductor to at least one of (1) impose a first voltage on the piezoelectric material or (2) have a voltage induced therein based on a movement of the piezoelectric material.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a processor (also referred to as a processor module) that may include a special purpose computer (i.e., created by configuring a processor) and/or a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (I) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C #, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor, processor module, module or 'controller' may be used interchangeably herein (unless specifically noted otherwise) and each may be replaced with the term 'circuit.' Any of these terms may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

Instructions may be executed by one or more processors or processor modules, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processor module" as used herein may refer to any of the foregoing structure or any other physical structure suitable for implementation of the described techniques. Also, the techniques could be fully implemented in one or more circuits or logic elements. The processor or processors may operate entirely automatically and/or substantially automatically. In automatic operation the processor may execute instructions based on received input and execute instructions in light thereof. Thus, various outputs may be made without further or any manual (e.g., user) input.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A tracking system, comprising:
a tracking assembly including:
    a composite member having at least a piezoelectric material, wherein the composite member is config-
ured to transduce in an ultrasound tracking system and an electromagnetic tracking system, and
a conductive coil electrically coupled to the piezoelectric material and configured to transmit a voltage to the piezoelectric material to cause the piezoelectric material to emit an ultrasound signal;
wherein the tracking assembly is configured to be associated with a tracked object.

2. The system of claim 1, wherein the conductive coil is formed of a coil of conductive material;
wherein the coil of conductive material is separate from the composite member.

3. The system of claim 1, wherein the conductive coil is formed of a coil of conductive material;
wherein the coil of conductive material is integral with the composite member.

4. The system of claim 1, wherein the composite member and the conductive coil are both wrapped around an axis of the tracked object.

5. The system of claim 4, wherein a first of the composite member or the conductive coil is wrapped over a second of the composite member or the conductive coil.

6. The system of claim 1, wherein the composite member is placed parallel to an axis of the tracked object.

7. The system of claim 1, wherein the composite member includes a conductor to at least one of (1) impose a first voltage on the piezoelectric material or (2) have a voltage induced therein based on a movement of the piezoelectric material.

8. The system of claim 7, wherein the composite member is configured to transduce an ultrasound signal;
wherein (1) the ultrasound signal is sensed by the composite member and the composite member imposes the second voltage on the conductor or (2) the first voltage causes a physical change in the piezoelectric material that generates the ultrasound signal.

9. The system of claim 1, further comprising:
an electromagnetic tracking system configured to track the tracking assembly;
an ultrasound tracking system configured to track the tracking assembly;
an ultrasound imaging device configured to emit an ultrasound imaging region;
wherein a tracked pose of the tracked object relative to a tracked pose of the ultrasound imaging region is operable to be determined at least by one of the electromagnetic tracking system or the ultrasound tracking system based on tracking the tracking assembly.

10. The system of claim 1, further comprising:
an ultrasound imaging device configured to emit an ultrasound imaging region and receive an ultrasound signal from the tracking assembly;
an electromagnetic tracking system configured to track the ultrasound imaging device;
wherein a tracked pose of the tracked object relative to a tracked pose of the ultrasound imaging region is operable to be determined at least by one of the electromagnetic tracking system or an ultrasound tracking system based on the received ultrasound signal from the tracking assembly.

11. A method to track an object, comprising:
providing a tracking assembly including:
    a composite member having at least a piezoelectric material, and
    a conductive coil electrically coupled to the piezoelectric material and configured to transmit a voltage to the piezoelectric material to cause the piezoelectric material to emit an ultrasound signal;

configuring the tracking assembly to be associated with the object and disposed on an exterior surface of the object.

12. The method of claim 11, further comprising:

forming the conductive coil of a coil of conductive material; and positioning the coil of conductive material separate from the composite member.

13. The method of claim 11, further comprising:

forming the conductive coil of a coil of conductive material; and forming the coil of conductive material integral with the composite member.

14. The method of claim 13, further comprising:

wrapping a first of the composite member or the conductive coil over a second of the composite member or the conductive coil.

15. The method of claim 11, further comprising:

wrapping both the composite member and the conductive coil around an axis of the instrument.

16. The method of claim 11, further comprising:

placing the composite member parallel to an axis of the instrument.

17. The method of claim 16, further comprising:

configuring the composite member to transduce an ultrasound signal including (1) sensing the second voltage imposed on the conductor by the composite member based on the ultrasound signal or (2) controlling a physical change in the piezoelectric material with the first voltage to generate the ultrasound signal.

18. The method of claim 11, further comprising:

providing the composite member with a conductor to at least one of (1) impose a first voltage on the piezoelectric material or (2) have a voltage induced therein based on a movement of the piezoelectric material.

19. The method of claim 11, further comprising:

tracking the tracking assembly with an electromagnetic tracking system;

tracking the tracking assembly with an ultrasound tracking system;

operating an ultrasound imaging device to emit an ultrasound imaging region; and determining a pose of the object relative to a tracked pose of the ultrasound imaging region at least by one of the electromagnetic tracking system or the ultrasound tracking system based on tracking the tracking assembly.

20. The method of claim 11, further comprising:

operating an ultrasound imaging device to emit an ultrasound imaging region and receive an ultrasound signal from the tracking assembly;

tracking the ultrasound imaging device with an electromagnetic tracking system;

determining a pose of the object relative to a tracked pose of the ultrasound imaging region at least by one of the electromagnetic tracking system or an ultrasound tracking system based on the received ultrasound signal from the tracking assembly.

21. A tracking assembly comprising a composite member and a conductive coil, wherein the composite member comprises:

a piezoelectric material;

a conductor electrically coupled to the piezoelectric material and configured to at least one of (1) impose a first voltage on the piezoelectric material or (2) have a voltage induced therein based on a movement of the piezoelectric material;

a support material that encases the piezoelectric material and the conductor; and a housing that surrounds the piezoelectric material, the conductor and the support material;

wherein the tracking assembly is configured to be associated with a tracked object and disposed on an exterior surface of the tracked object.

* * * * *